US009206531B2

(12) United States Patent
Inoue et al.

(10) Patent No.: US 9,206,531 B2
(45) Date of Patent: Dec. 8, 2015

(54) IODINE- AND AMYLOSE-CONTAINING FIBERS, METHOD FOR PRODUCTION THEREOF, AND USE THEREOF

(75) Inventors: Osamu Inoue, Hyogo (JP); Masatoshi Yoshikawa, Hyogo (JP); Mieko Takaku, Hyogo (JP); Tatsuo Kaiho, Tokyo (JP); Mitsuru Taguchi, Tokyo (JP); Haruyo Sambe, Osaka (JP); Yoshinobu Terada, Osaka (JP); Takeshi Takaha, Osaka (JP)

(73) Assignees: Kanto Natural Gas Development Co., Ltd., Tokyo (JP); Omikenshi Co., Ltd., Osaka (JP); Ezaki Glico Co., Ltd., Osaka (JP)

( * ) Notice: Subject to any disclaimer, the term of this patent is extended or adjusted under 35 U.S.C. 154(b) by 320 days.

(21) Appl. No.: 13/378,407
(22) PCT Filed: Jun. 17, 2010
(86) PCT No.: PCT/JP2010/004069
§ 371 (c)(1),
(2), (4) Date: Mar. 21, 2012
(87) PCT Pub. No.: WO2010/146875
PCT Pub. Date: Dec. 23, 2010

(65) Prior Publication Data
US 2012/0183491 A1    Jul. 19, 2012

(30) Foreign Application Priority Data

Jun. 18, 2009    (JP) ................................. 2009-145769
Feb. 8, 2010    (JP) ................................. 2009-026001

(51) Int. Cl.
*D01F 2/08*    (2006.01)
*D06M 11/09*    (2006.01)
(Continued)

(52) U.S. Cl.
CPC *D01F 2/08* (2013.01); *A01N 59/12* (2013.01); *A61K 8/00* (2013.01); *A61L 9/01* (2013.01); *D06M 11/09* (2013.01); *D06M 16/00* (2013.01); *D06M 2101/06* (2013.01)

(58) Field of Classification Search
None
See application file for complete search history.

(56) References Cited

U.S. PATENT DOCUMENTS 4,144,079 A    3/1979    Smith
2007/0251021 A1*    11/2007    Schopke et al. ............... 8/115.6

FOREIGN PATENT DOCUMENTS

CN    1946895 A    4/2007
JP    61-500500    3/1986
(Continued)

OTHER PUBLICATIONS

"Amylose and Amylopectin" article (Seventeenth Report of the Joint FAO/WHO Expert Committee on Food Additives, Wld Hlth Org. techn. Rep. Ser., 1974, No. 539; FAO Nutrition Meetings Report Series, 1974, No. 53.*
(Continued)

*Primary Examiner* — Carlos Azpuru
*Assistant Examiner* — Casey Hagopian
(74) *Attorney, Agent, or Firm* — Renner, Otto, Boisselle & Sklar, LLP

(57) ABSTRACT

A method for producing an amylose-containing rayon fiber, comprising the steps of: mixing an aqueous alkaline solution of amylose with viscose to obtain a mixed liquid, spinning the mixed liquid to obtain an amylose-containing rayon fiber, and bringing the amylose-containing rayon fiber into contact with iodine or polyiodide ions, thereby allowing an amylose in the amylose-containing rayon fiber to make a clathrate including the iodine or polyiodide ions, wherein the amylose is an enzymatically synthesized amylose having a weight average molecular weight of $3\times10^4$ or more and $2\times10^5$ or less. A method for collecting iodine from brackish water with high efficiency utilizing the amylase-containing rayon fibers.

18 Claims, 3 Drawing Sheets

(51) Int. Cl.
- *D06M 16/00* (2006.01)
- *D06M 101/06* (2006.01)
- *A01N 59/12* (2006.01)
- *A61L 9/01* (2006.01)
- *A61K 8/00* (2006.01)

(56) References Cited

FOREIGN PATENT DOCUMENTS

| | | |
|---|---|---|
| JP | 11-124721 | 5/1999 |
| WO | 85/02422 | 6/1985 |

OTHER PUBLICATIONS

International Search Report for corresponding International Application No. PCT/JP2010/004069 mailed Jul. 13, 2010.
Form PCT-ISA-237 for corresponding International Application No. PCT/JP2010/004069 dated Jul. 13, 2010.
Office Action issued in corresponding Chinese Application No. 201080026607.7 dated Jan. 20, 2014 and English translation.
Notification to Make Divisional Application issued in corresponding Chinese Application No. 201080026607.7 dated Oct. 29, 2013.
Ezaki Glico Co., Ltd., "Amylase Synthesized by The Enzymatic Method, A New Material Synthesized for The First Time in The World and The Wide Use Thereof", Biobusiness, Issue 5, Dec. 31, 2006, pp. 66-67.

* cited by examiner

IODINE- AND AMYLOSE-CONTAINING FIBERS, METHOD FOR PRODUCTION THEREOF, AND USE THEREOF

TECHNICAL FIELD

The present invention relates to an amylose-containing functional rayon fiber, a method for producing thereof, and use thereof.

BACKGROUND ART

A plant starch is composed of amylase and amylopectin. For example, a usual corn starch is composed of about 20% of amylose and about 80% of amylopectin. Natural amylose contained in the plant starch is a polysaccharide in which many glucoses are mainly bound through α-1,4-glucoside bonds, and it is known that a small amount of branch structures composed of an α-1,6-glucoside bond are also contained. On the other hand, amylopectin is a macromolecule in which a lot of short amylose chains with a degree of polymerization of about 20 are bound through α-1,6-glucoside bonds in a tufted shape. It has been known for a longtime that a linear α-1,4-glucan chain constituting an amylose has a feature of forming a helical structure, and has a function of incorporating various substances into inside of the helical structure (referred to as clathrate function). It has been apparent that blue color developed by the addition of an iodine solution to a starch (iodine-starch reaction) is caused by making a clathrate including iodine atoms inside of an amylose helical structure. There are known, as a substance which can be made to be clathrate by amylose, many inorganic molecules and organic compounds, such as fatty acids and surfactants, in addition to iodine.

Amylose is a polysaccharide having a unique function of clathrate function. However, since it is very difficult to separate amylose from amylopectin in a starch, production of pure amylose is not performed in an industrial scale, and industrial use of amylose is not being advanced. It has recently become possible to enzymatically synthesize pure amylose (Patent Document 1), and a study regarding use of amylose has being proceeding (Patent Document 2). For example, Patent Document 3 discloses molded articles such as fibers and films made of an enzymatically synthesized amylose. These molded articles made of amylase are excellent in biodegradability and biocompatibility since they are easily degraded by amylase in microorganisms or in the body of an animal. Therefore, Patent Document 3 discloses use of molded articles made of amylose in applications which require biodegradability. However, these fibers made only of amylose are not suited for repeated use or applications such as those in which washing is repeated, because of the very high biodegradability. It is described that biodegradability can be controlled by chemical modification. However, chemical modification remarkably suppresses the clathrate function of amylose, these fibers are not suited for use in applications in which the clathrate function of amylose is utilized.

At present, chemical fibers such as polyester fibers are mainly used as fibers. However, since amylose cannot be dissolved in a solvent for materials of conventional chemical fibers, amylose cannot be contained in chemical fibers. Even if being contained is possible, since chemical fibers are not compatible with amylose, they cannot be mixed in a molecular level, and thus causing phase separation.

On the other hand, cellulose is a polysaccharide constituting plant cell walls and in which many glucoses are linked through β-1,4-glucoside bonds. Cellulose is a polysaccharide which is by far excellent in stability as compared with a starch, and it is a main raw material for, for example, clothing, nonwoven fabric, paper and the like.

If it is possible to impart the clathrate function of amylose to cellulose, there is a possibility that a novel functional material having features of both substances can be developed. Patent Document 4 discloses a method in which cellulose fibers are coated with amylose by applying an aqueous amylose solution to a nonwoven fabric made of cellulose fibers. This method is easy to operate and is practical. However, this method has a problem that the product also cannot endure repeated use since amylose attached on the cellulose surface is easily lost by an operation such as washing.

One of cellulose fibers includes rayon. Rayon is fiber which is formed while regenerating cellulose from a solution (viscose) which is prepared by dissolving cellulose using carbon disulfide. Due to the feature in their production, rayon has such a feature that various functional substances can be contained in rayon by adding these functional substances to viscose, and thus making it possible to impart functions to the rayon. There have hitherto been disclosed rayon fibers containing chitosan (Patent Document 5), rayon fibers containing complex metal oxide microparticles (Patent Document 6), rayon fibers containing bincho-tan charcoal microparticles (Patent Document 7), rayon fibers containing an anionic macromolecule (Patent Document 8), and the like. However, when rayon is produced by adding a functional substance to viscose, the functional substance is coated with the rayon fibers, and thus the expected functionality can not be sufficiently used in some cases. In contrast, the shape of a functional component has been devised so as to expose the functional component on the surface of rayon fibers (Patent Document 7). However, this method is not necessarily applicable to any functional component. There has been another devise such as reduction processing treatment of exposing a functional component by decomposing cellulose on the surface of rayon fibers using an enzyme (Patent Document 6). However, this method also has problems such as deterioration of texture of the rayon fibers and a decrease in mechanical strength of the rayon fiber. There is also a problem such as deterioration of washing resistance caused by exposure of the functional component.

Patent Document 8 discloses that, when a macromolecular substance is contained in rayon, the molecular weight of the macromolecular substance is suitably from 10,000 to 500,000 from the viewpoint of yield of remaining in a rayon. However, the technique described in Patent Document 8 merely uses the macromolecular substance so as to retain ionic functional groups in rayon, and the structure of the macromolecular substance in the rayon is not an issue. When a macromolecular substance such as amylose has a function, in addition to that the function is not exerted because of the macromolecular substance is coated with rayon as described above, due to the structural change of the macromolecular substance and the like, the function may not be sufficiently exerted. It is very difficult to predict the results since the structural change of the macromolecular substance varies depending on the kind of and the production method of the macromolecular substances. It is known that the structure of the macromolecular substance, rather, changes easily by physiochemical stimulation, and thus it is considered that the function of the macromolecular substance is lost as a result of the structural change caused by being contained in rayon. Furthermore, Patent Document 8 aims at preventing the antimicrobial effect from reducing by loss of a quaternary ammonium salt compound during repeated washing, and therefore the object of Patent Document 8 is quite different from that of the present invention. An antimicrobial agent binds through an ionic bond in the method described in Patent Document 8, whereas, in the present invention, an antimicrobial agent is made to be clathrate in amylose. Therefore, these techniques of retaining the antimicrobial agent are completely different. Furthermore, ionic bonds can bond the antimicrobial agent only to a portion where an ion is present, whereas, in the present invention, the antimicrobial agent can be made clathrate in various portions of the amylose chain. Therefore, the antimicrobial agent can be bound in an amount larger than that in a conventional manner if the content of the substance to be bound to a quaternary ammonium salt in the fiber is the same as the content of amylose.

Cyclodextrin is known as a compound having ability to form a clathrate. However, since cyclodextrin has a low molecular weight and is dissolved in water, in the case of viscose rayon made by a wet spinning method, cyclodextrin is eluted in a spinning bath during forming into fibers, and thus the yield of retaining in the fibers is not high. Even if a small amount of cyclodextrin can be contained in the rayon fibers, the cyclodextrin is eluted easily from the fibers, and thus the obtained fibers are inferior in stability.

Therefore, there is disclosed a method in which cyclodextrin is bound to the fiber surface through a chemical bond (Non-Patent Document 1). However, this method can impart the ability to form a clathrate only to the fiber surface. There is also a problem that when the fibers are, for example, exposed to an acid or alkaline solution, the chemical bond is cleaved to elute cyclodextrin on the fiber surface and the ability to form a clathrate is easily lost.

There is disclosed, as a method of allowing fibers to contain cyclodextrin, a method in which a conjugate obtained by bonding cyclodextrin to the end of a polyester-based polymer through a chemical bond is mixed with a thermoplastic resin to obtain fibers (Patent Document 10). However, cyclodextrin is bound only to the end of the polymer and thus the amount of bound cyclodextrin is small, and cyclodextrin coated with the polymer cannot exhibit the ability to form a clathrate. Therefore, there is a problem that the clathrate amount of a guest substance is limited. If it is tried to increase the amount of bound cyclodextrin by this method, the degree of polymerization of the polymer has to be lowered, and, as a result, causing a problem that the fiber strength is insufficient. In contrast, there is also disclosed a method in which a plural of cyclodextrins are chemically bound to a polymer molecule (Patent Document 11). However, this method requires complicated steps of synthesizing a cyclodextrin derivative and then polymerizing the cyclodextrin derivative, leading to much labor in synthesis and poor efficiency. Furthermore, it is unclear whether or not the obtained polymer can be formed into fibers and the obtained fibers have sufficient ability to form a clathrate after molding.

As described above, it becomes necessary that a polymer substance having ability to form a clathrate, such as amylose is contained in the entire fibers so as to impart the ability to form a clathrate to the entire fibers. However, there are many problems to be solved, including a loss of the ability to form a clathrate of amylose caused by being contained into the fibers, and a change in physical properties of the fibers caused by containing of amylose.

When amylose is used as a functional component, natural amylose cannot be completely dissolved under an alkaline condition at the time of the production of rayon, even if it is tried to add the natural amylose into rayon in the same method as in Patent Documents 5 to 8. As a result, an amylose-containing rayon can not be produced because of the occurrence of nozzle clogging or the like at the time of the production of rayon.

On the other hand, with respect to a method of producing iodine, there are known, as a method of obtaining iodine from brine or the like, a blowing-out method in which iodide ions, an iodine compound and the like are converted into iodine molecules by chemical reaction or the like, and the iodine molecules are vaporized out into the air and then recovered by absorbing with an absorption liquid; an activated carbon adsorption method in which iodine is recovered by adsorbing with activated carbon; copper and silver methods in which iodine is reacted with copper or silver and then recovered as a precipitate of copper iodide or silver iodide; an ion exchange resin adsorption method in which iodide ions are converted into iodine molecules or polyiodide ions, and then the iodine molecules or polyiodide ions are recovered by adsorbing with an ion exchange resin; and the like.

Among these methods, a blowing-out method and an ion exchange resin adsorption method are mainly used. However, there is a problem that the collection ratio of iodine is from 80 to 90% and iodine remains in the brine although in a low concentration after iodine collection, together with dissolved matters such as ammonia and bromine. In the ion exchange resin adsorption method, there is a method that a large amount of an alkali is required when detaching iodide ions from the resin, and thus causing deterioration of the resin. Furthermore, any of these conventionally known methods have a problem that complicated steps are required. Therefore, it has been desired to provide a method of adsorbing and recovering iodine, which consists of simple steps and can adsorb almost 100% of iodine from brine, and can also recover and industrially use the adsorbed iodine.

There have hitherto been disclosed, as a substance capable of stably retaining iodine, for example, an amylose powder (Patent Document 4) and a CD polymer (Patent Document 9).

It is known that iodine is made clathrate in amylose (for example, Patent Document 4). However, it is not possible to use those, in which iodine is made clathrate in an amylose powder, for the purpose of recovering iodine from brine since iodine is released from them in an aqueous solution.

Furthermore, in order to retaining iodine by stably making clathrate in an amylose powder, a metal halide is required. The metal halide is easily lost from the amylose powder. Therefore, when the amylose powder retaining iodine is used in a molded article, there may arise a problem of lowering of retaining stability of iodine due to lose of metal halide.

Patent Document 9 discloses a method in which a CD polymer is used as an iodine adsorption material. However, the CD polymer has problems such as low adsorption capacity and higher cost compared to an ion exchange resin. Furthermore, the CD polymer can retain iodine only in the form of triiodide ions ($I_3^-$). The properties of iodine, such as antimicrobial and oxidation potencies, are exerted in the form of iodine molecules ($I_2$). Therefore, in the CD polymer, the proportion of the iodine molecules ($I_2$) of the entire iodine is low, such as ⅔, and thus there is a problem of low retaining amount of effective iodine ($I_2$) and a problem of poor retaining stability. It is expected that substances retaining iodine molecules are used under a high humidity environment, such as disposable masks, for the purpose of exerting their antimicrobial property and oxidation potency. It is noted that masks are referred to as face masks or hospital masks in English. However, the conventional CD clathrate substances are said to release iodine molecules by humidification, and thus safety for humans arising from inhaling the iodine molecules is also an issue to be concerned.

As described above, there have been required to provide molded articles which can retain iodine in the state of iodine molecules or polyiodide ions without adding metal halide. There have also been required to provide molded articles which can retain iodine stably even under a high humidity environment.

PRIOR ART DOCUMENTS

Patent Documents

[Patent Document 1] Japanese National Phase PCT Laid-Open Publication No. 2004-526463
[Patent Document 2] International Publication No. WO 2006/082968 Pamphlet
[Patent Document 3] International Publication No. WO 02/006507 Pamphlet
[Patent Document 4] Japanese Laid-Open Publication No. 2008-37833
[Patent Document 5] Japanese Laid-Open Publication No. 8-92820
[Patent Document 6] Japanese Laid-Open Publication No. 2004-162245
[Patent Document 7] Japanese Laid-Open Publication No. 2001-98412
[Patent Document 8] Japanese Laid-Open Publication No. 7-173711
[Patent Document 9] Japanese Laid-Open Publication No. 2008-93545
[Patent Document 10] Japanese Laid-Open Publication No. 2005-503476
[Patent Document 11] Japanese Laid-Open Publication No. 08-100027

Non-Patent Documents

[Non-Patent Document 1] Journal of Inclusion Phenomena and Macrocyclic Chemistry, vol. 25, pp. 197-202, 1996

SUMMARY OF THE INVENTION

Problems to be Solved by the Invention

The present invention is intended to solve the above-mentioned problems.

Means for Solving the Problems

An object of the present invention is to develop fibers imparted with the clathrate function of amylose, and more specifically to develop functional rayon fibers imparted with the clathrate function of amylose. The functional rayon fibers of the present invention does not cause a large change in physical properties of the rayon fibers, except for being imparted with the clathrate function of amylose, and stably retains amylose, and also it does not substantially cause elution of amylose during an operation such as washing, and thus enduring repeated use. Furthermore, since the functional rayon fibers of the present invention contains amylose in the state capable of exerting the clathrate function, additional functions can be imparted to the fiber by bringing the fibers into contact with various guest substances and making the substances to be clathrate in the amylose. The functional rayon fibers of the present invention also make it possible to efficiently recover iodine from brine. The functional rayon fibers of the present invention can also stably retain iodine or polyiodide ions, regardless of the presence or absence of a metal halide.

The present inventors conducted intensive studies in order to solve the aforementioned problems, and, as a result, found that rayon is most suitable for obtaining fibers imparted with the clathrate function of amylose. They have found that it is possible to produce amylose-containing rayon fibers, in which amylose is not substantially eluted and amylose is dispersed in the rayon fibers in the state capable of exerting the clathrate action, by mixing an enzymatically synthesized amylose dissolved in an alkali with viscose, thereby dispersing the amylose in the mixture, and forming the mixture into fibers during the process of producing rayon fibers, and thus the present invention has been completed based on the findings. The obtained fibers scarcely cause a large change in original physical properties of rayon fibers, except for being imparted with the clathrate function of amylose. In particular, use of a complete linear amylose having an average molecular weight of about $3 \times 10^4$ or more and about $2 \times 10^5$ or less enables the rayon fibers to contain amylose in the state of maintaining the ability to form a clathrate. Furthermore, since the amylose-containing rayon fibers of the present invention stably retains amylose, the amylose-containing rayon fibers of the present invention have a remarkable effect capable of enduring repeated use. Furthermore, the clathrate function of amylose can be further enhanced in rayon by subjecting the rayon fibers of the present invention to a heat treatment in an aqueous solution containing an organic solvent. As described above, the present inventors have completed the present invention by developing functional rayon fibers having excellent characteristics that have never been achieved heretofore, and a method for producing the same.

For example, the present invention provides the followings:

(Item 1) A method for producing an amylose-containing rayon fiber, comprising the steps of:
mixing an aqueous alkaline solution of amylose with viscose to obtain a mixed liquid;
spinning the mixed liquid to obtain an amylose-containing rayon fiber; and
bringing the amylose-containing rayon fiber into contact with iodine or polyiodide ions, thereby allowing an amylose in the amylose-containing rayon fiber to make a clathrate including the iodine or polyiodide ions; wherein
the amylose is an enzymatically synthesized amylose having a weight average molecular weight of about $3 \times 10^4$ or more and about $2 \times 10^5$ or less.

(Item 2) The method according to Item 1, wherein the amylose-containing rayon fiber is subjected to a heating treatment and cooling treatment before bringing into contact with the iodine or polyiodide ions.

(Item 3) The method according to Item 1 or 2, wherein the amylose-containing rayon fiber is subjected to an alkaline treatment before bringing into contact with the iodine or polyiodide ions.

(Item 4) The method according to any one of Items 1 to 3, wherein the enzymatically synthesized amylose is an amylose which does not contain a α-1,6-glucoside bond.

(Item 5) The method according to any one of Items 1 to 4, wherein the enzymatically synthesized amylose has a polydispersity of about 3.0 or less.

(Item 6) The method according to any one of Items 1 to 5, wherein the content of the enzymatically synthesized amylose in the amylose-containing rayon fiber is about 0.01% by weight or more and about 50% by weight or less.

(Item 7) An amylose-containing rayon fiber, wherein amylose in the rayon fiber is not substantially eluted by washing and is dispersed in the rayon fiber in a state capable of exerting the clathrate action; and wherein the amylose is an enzymatically synthesized amylose having a weight average molecular weight of about $3\times10^4$ or more and about $2\times10^5$ or less, and the amylose includes iodine or polyiodide ions.

(Item 8) The amylose-containing rayon fiber according to Item 7, wherein the content of the amylose is about 0.01% by weight or more and about 50% by weight or less.

(Item 9) The amylose-containing rayon fiber according to Item 7 or 8, wherein the enzymatically synthesized amylose is an amylose which does not contain an α-1,6-glucoside bond.

(Item 10) The amylose-containing rayon fiber according to anyone of Items 7 to 9, wherein the enzymatically synthesized amylose has a polydispersity of about 3.0 or less.

(Item 11) The amylose-containing rayon fiber according to any one of Items 7 to 10, wherein the content of a metal halide is 0.1-fold moles or less of the content of iodine molecules ($I_2$).

(Item 12) A deodorant product comprising the amylose-containing rayon fiber according to any one of Items 7 to 11.

(Item 13) A antimicrobial product comprising the amylose-containing rayon fiber according to any one of Items 7 to 11.

(Item 14) A method for trapping iodine or polyiodide ions in a fiber so as to concentrate, recover, remove or isolate the iodine or polyiodide ions, the method comprising the steps of:
bringing an amylose-containing rayon fiber into contact with iodine or polyiodide ions, thereby allowing an amylose in the amylose-containing rayon fiber to make a clathrate including the iodine or polyiodide ions,
wherein the amylose-containing rayon fiber is obtained by a method comprising the steps of:
mixing an aqueous alkaline solution of amylose with viscose to obtain a mixed liquid; and
spinning the mixed liquid to obtain an amylose-containing rayon fiber; and
the amylose is an enzymatically synthesized amylose having a weight average molecular weight of about $3\times10^4$ or more and about $2\times10^5$ or less.

Effects of the Invention

The amylose-containing rayon fibers of the present invention stably retains amylose, and does not substantially cause elution of amylase during an operation such as washing, and thus it is possible to endure repeated use. Furthermore, the amylose-containing rayon fibers contain amylose in the state capable of exerting the clathrate function, and additional functions can be imparted to the fiber by adding various guest substances. Utilization of the material makes it possible to efficiently recover iodine from brine. Furthermore, the amylose-containing rayon fibers in which iodine being a clathrate exert quite excellent microbiocidal and deodorant functions.

MODE FOR CARRYING OUT THE INVENTION

Figure 1:
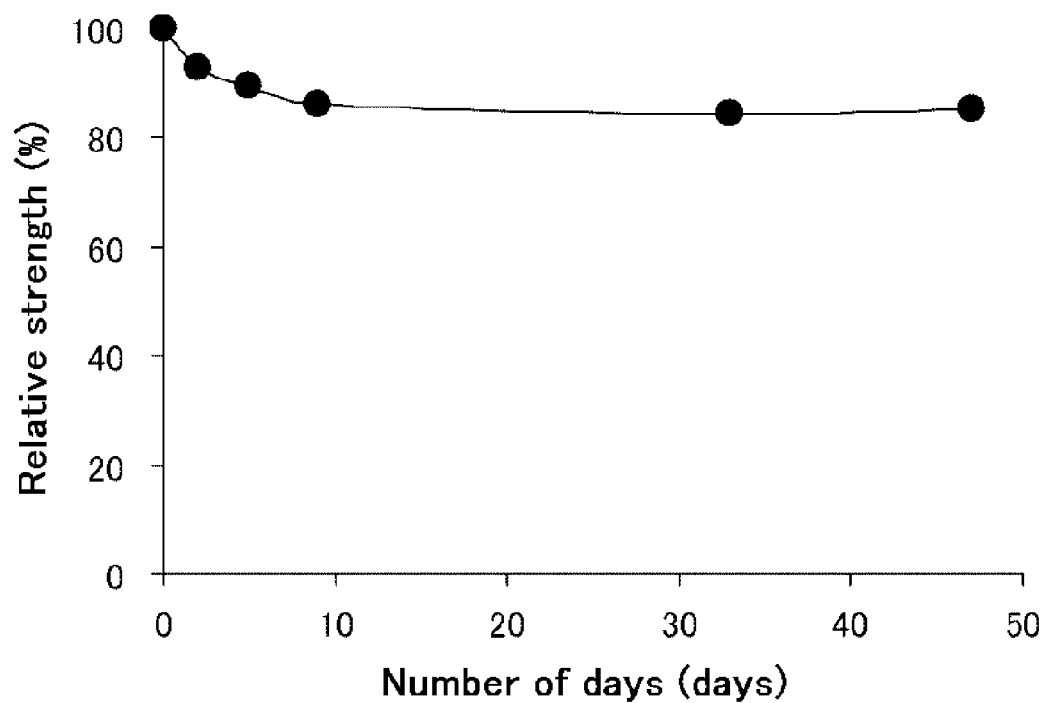
FIG. 1 is a graph showing a result of examining the amount of iodine in an iodine clathrate amylose-containing nonwoven rayon fabric obtained in Example 7 over time. The vertical axis denotes relative intensity, while the horizontal axis denotes number of days (days).

The present invention will be described in detail below.
(1. Materials)
(1.1) Amylose
As used in the present specification, "amylose" refers to a saccharide in which D-glucose is a constitutional unit, and which is a substantially linear polysaccharide having at least two sugar units linked mainly through an α-1,4-glucoside bond. In the amylose molecules used in the present invention, the saccharide units are preferably linked only by the α-1,4-glucoside bond. The term "linear" refers to the state where branches are absent. Branches are formed by, for example, a structure in which glucose residues are linked at three positions of the position 1, the position 4 and the position 6 of one glucose residue. The term "substantially linear" includes both complete linear molecules and linear molecules containing a small amount of branches. The number of branches is preferably about 100 or less, more preferably about 50 or less, still more preferably about 10 or less, particularly preferably about 1 or less, and most preferably 0 per 10,000 glucose residues. Amylose is synonymous to linear α-glucan and α-1,4-glucan. Among the linear amylose, amylose with no branches is referred to as a complete linear amylose.

Amylose may contain α-1,6-glucoside bonds in a relatively small number. In the amylose used in the present invention, the number of the α-1,4-glucoside bonds is preferably about 100 or more, more preferably about 200 or more, still more preferably about 300 or more, particularly preferably about 400 or more, and most preferably about 500 or more, when assuming that the number of the α-1,6-glucoside bond is 1. In the amylose used in the present invention, preferably, there is no specific upper limit on the number of the α-1,4-glucoside bonds when assuming that the number of the α-1, 6-glucoside bond is 1, and the number of α-1,4-glucoside bonds can be for example, about 15,000 or less, about 10,000 or less, about 5,000 or less, about 4,000 or less, about 3,000 or less, about 2,000 or less, about 1,000 or less, about 500 or less, about 400 or less, about 300 or less, or the like.

The polydispersity of the amylase used in the present invention is preferably 3.0 or less. Macromolecular compounds do not have a single molecular weight but have a certain variation in molecular weight regardless of whether it is naturally-occurring or not, except for special cases such as protein. Therefore, to represent a degree of dispersion of molecular weight of macromolecular compounds, polydispersity, Mw/Mn, is generally used in the field of macromolecular chemistry. Polydispersity, Mw/Mn, is represented as a ratio of weight average molecular weight "Mw" to number average molecular weight "Mn" (i.e., Mw/Mn). Polydispersity is an indicator of the breadth of the molecular weight distribution of macromolecular compounds. When a macromolecular compound has a completely single molecular weight, Mw/Mn is equal to 1, and when a macromolecular compound has a wider molecular weight distribution, the macromolecular compound has a lager Mw/Mn than 1.

The polydispersity of the amylase used in the present invention is more preferably about 2.8 or less, and further more preferably about 2.5 or less, further more preferably about 2.3 or less, further more preferably about 2.0 or less, further more preferably about 1.5 or less, and most preferably about 1.2 or less.

The number of saccharide units contained in one molecule of α-1,4-glucan is referred to as a degree of polymerization. In the present specification, the term "degree of polymerization" refers to a weight average degree of polymerization unless otherwise specified. In the case of α-1,4-glucan, the weight average degree of polymerization is calculated by dividing the weight average molecular weight by 162. In the present specification, the term "average molecular weight" refers to a weight average molecular weight unless otherwise specified.

Natural starch is usually composed of a mixture of both amylose (a polymer having a structure in which glucose is linearly bound) and amylopectin (a tufted polymer in which amylose has branching). Amylose contained in natural starch usually has a molecular weight distribution (Mw/Mn) wider than 3.0 and, and since (i) a low molecular weight amylose which is easily crystallized, (ii) a high molecular weight amylose which is easily dissolved in water, and (iii) amylose having a middle molecular weight which is easily gelled coexist, they mutually inhibit excellent amylose characteristics in another molecular weight region. Furthermore, natural amylose may often contain a small amount of branches. Due to these causes, when amylose isolated from natural starch is used, the obtained product has poor characteristics. When an alkali solution with high concentration is prepared using the high molecular weight amylose, the viscosity of the alkali solution increases, and thus the processing characteristics of the alkali solution become inferior, for example, in the production of fibers. Therefore, natural amylose is not preferable. In other words, amylose other than natural amylose is preferably used in the present invention.

The amylose used in the present invention is preferably an enzymatically synthesized amylose. The enzymatically synthesized amylose refers to amylose obtained by linking the saccharide units to the primer utilizing an enzyme. The enzymatically synthesized amylose used in the present invention can be produced by any enzymatic synthesis method known in the art. Examples of such enzymatic synthesis method include a method using glucan phosphorylase. Phosphorylase is an enzyme that catalyze a phosphorolytic reaction. Examples of the enzymatic synthesis method of amylose that can be used in the present invention include the followings:

(1) a method in which an α-1,4-glucan chain is synthesized by transferring a glucosyl group in α-glucose-1-phosphate to a primer maltoheptaose or the like by α-glucan phosphorylase (Glucan phosphorylase; GP) (for example, derived from a potato);

(2) a method in which an α-1,4-glucan chain is synthesized by allowing sucrose phosphorylase and glucan phosphorylase simultaneously to act using a primer, sucrose and inorganic phosphoric acid or glucose-1-phosphate as a substrate (hereafter referred to as an SP-GP method) (Waldmann H. et al., Carbohydrate Research, 157 (1986) c4-c7; WO2002/097107). This method having an advantage that the linear glucan can be synthesized in more inexpensively as compared with other methods; and (3) a method in which an α-1,4-glucan chain is synthesized by allowing amylosucrase to act using a primer and sucrose as substrates.

The "primer" used in the production of the enzymatically synthesized amylose refers to a saccharide chain molecule, which serves as a starting material in the synthesis of an α-1,4-glucan chain. Examples of the primer include any saccharide to which a saccharide unit can be added by α-glucan phosphorylase. Examples of the primer include malto-oligo saccharide.

A method of producing an enzymatically synthesized amylose is described in Japanese National Phase PCT Laid-Open Publication No. 2004-526463. The enzymatically synthesized amylose has such advantages as containing no branches and having low polydispersity, i.e., having uniform molecular weights.

The average molecular weight (weight average molecular weight) of the amylase used in the present invention is preferably about $3 \times 10^4$ or more, more preferably about $4 \times 10^4$ or more, particularly preferably about $4.5 \times 10^4$ or more, and most preferably about $5 \times 10^4$ or more, in order to realize the property of having ability to form a clathrate while the amylose is contained in rayon. The average molecular weight of the amylose used in the present invention is preferably about $2 \times 10^5$ or less, more preferably about $1.5 \times 10^5$ or less, and most preferably about $1.2 \times 10^5$ or less.

When the average molecular weight of the amylose is too low, there occurs a problem that the ability of the amylase to form a clathrate is not sufficiently exerted in rayon. When the average molecular weight of the amylose is too high, the amylose may not be satisfactorily incorporated into rayon, the ability of the amylase to form a clathrate may be damaged, or the filterability of viscose may deteriorate, and thus it may become difficult to stably produce rayon fibers.

The average molecular weight of the enzymatically synthesized amylose can be adjusted by changing the ratio of the concentration of the sucrose to the concentration of the primer used in enzymatic synthesis. When the concentration of the sucrose is constant, as the concentration of the primer is lower, the average molecular weight of the amylase to be obtained is larger. Those skilled in the art can easily synthesize amylose having the objective molecular weight by reading Patent Document 1 and Synthesis Examples of the present application.

(1.2) Rayon Fiber Raw Material

Any viscose known in the art can be used as a rayon fiber raw material. Viscose can be produced by a known method in the art. For example, sulfite pulp is immersed in a 17 to 18% caustic soda solution. The pulp is converted into alkali cellulose and the volume increases to 4 to 5 times. The alkali cellulose is compressed to squeeze off the excessive alkali and crushed in a crusher, followed by agitation. The obtained substance is aged and then reacted with carbon disulfide to form xanthate. A liquid obtained by adding diluted caustic soda solution to xanthate to form into a liquid is referred to as viscose.

(1.3) Substance to be Made Clathrate

In the invention of the present application, the substance to be made clathrate in amylose (also referred to as a guest substance) can be any substance as long as it can be made clathrate in amylose. The guest substance can be a molecule, compound, atom, ion or the like. In a specific embodiment, the guest substance is iodine or polyiodide ions. Other substances other than iodine or polyiodide ions may be simultaneously made clathrate.

Examples of the guest substance include (a) microbicides and antimicrobial agents; (b) insect proofing components; (c) odor components; (d) components to be stabilized; (e) sustainably released components; (f) ultraviolet absorbing substances; (g) cosmetic components; (h) colorants or dyes; (i) deodorant components and (j) anti-molding components.

Examples of the (a) microbicides and antimicrobial agents include, for example, antimicrobial drugs such as iodine, polyiodide ions (for example, triiodide ions), penicillin, Ampicillin, amoxicillin, cephalosporin, tetracycline, oxytetracycline, chlortetracycline, methicillin, colistin sulfomethate sodium, carbenicillin sodium, gentamicin, erythromycin, azithromycin, roxithromycin, clarithromycin, telithromycin, josamycin, spiramycin, leucomycin, midecamycin, rokitamycin, midecamycin, tobramycin, kanamycin, cefuroxime sodium, meropenem, netilmicin, sisomicin, Ceftibuten, tobramycin, doxorubicin, astromicin, cefetametpivoxil, nalidixic acid, piromidic acid, pipemidic acid, cinoxacin, norfloxacin, ofloxacin, enoxacin, ciprofloxacin, tosufloxacintosilate, lomefloxacin, sparfloxacin, fleroxacin, levofloxacin, gatifloxacin, prulifloxacin, vancomycin, chloramphenicol, and salts thereof; parabens such as methylparaben, ethylparaben, propylparaben, butylparaben, and benzylparaben; cationic microbicides such as alkyldimethyl benzalkonium, alkyldimethyl benzethonium, quaternary ammoniums such as dialkyl dimethyl ammonium and polidronium, and salts thereof; alkylpyridiniums such as cetylpyridinium, and salts thereof; biguanide-based compounds such as chlorhexidine, and salts thereof; amphoteric surfactants having an alkyl side chain, such as alkyldiaminoethylglycine and alkylpolyaminoethylglycine; nonionic microbicides such as triclosan, glutaraldehyde, and polyhexamethylene guanide; isothiazoline-based compounds such as 4,5-dichloro-2-octyl-4-isothiazolin-3-one and 2-octyl-4-isothiazolin-3-one; imidazole-based compounds such as methyl 2-benzoimidazole carbamate, 2-(4-thiazolyl)-benzimidazole; organoiodine-based compounds such as 3-iodo-2-propynyl-butyl-carbamate, diiodomethyl-p-tolyl-sulfone, p-chlorophenyl-3-iodopropargylformal, and 2,3,3-triiodoallyl alcohol; thiophene-based compounds such as 3,3,4,4-tetrachlorotetrahydrothiophene-1,1-dioxide; triazole-based compounds such as 1-[[2-(2,4-dichlorophenyl)-1,3-dioxan-2-yl]methyl]-1H-1,2,4-triazole, (±)-α[2-(4-chlorophenyl) ethyl]-α-(1,1-dimethylethyl)-1H-1,2,4-triazole-(1)-ethanol, and (±)-1-[2-(2,4-dichlorophenyl)-4-propyl-1,3-dioxan-2-ylmethyl]-1H-1,2,4-triazole; urea-based compounds such as 3-(3,4-dichlorophenyl)-1,1-dimethylurea; triazine-based compounds such as 2-methylthio-4-tert-butylamino-6-cyclopropynylamino-s-triazine; oxathiazine-based compounds such as 3-benzo[b]thien-2-yl-5,6-dihydro-1,4,2-oxathiazine-4-oxide; alcohol-based compounds such as 2,2-dibromo-2-nitroethanol and 2-bromo-2-nitropropane-1,3-diol; and the like.

Examples of the (b) insect proofing components include, for example, iodine, polyiodide ions (for example, triiodide ions), pyrethroid-based insect proofing agents suchaspyrethrin, cinerin, jasmoline, empenthrin, allethrin, phenothrin, tellallethrin, prallethrin, phthalthrin, resmethrin, furamethrin, phenothrin, permethrin, cypermethrin, cyphenothrin, veratorine, ethofenprox, cyfluthrin, tefluthrin, bifenthrin, fenvalerate, imiprothrin, transfluthrin, fenpropathrin, and fenfluthrin; paradichlorobenzene, naphthalin, camphor, DEET, herbal extract, wasabi extract, *capsicum* extract, *perilla* extract, tea extract and the like.

Examples of the (c) odor components include, for example, aromatic components and malodorous components.

Examples of the aromatic components include, for example, natural perfumes such as musk, civet, ambergris, Abies oil, ajwain oil, almond oil, *angelica* root oil, basil oil, bergamot oil, birch oil, Bois de Rose oil, cajeput oil, *cananga* oil, *capsicum* oil, caraway oil, cardamom oil, *cassia* oil, celery oil, cinnamon oil, citronella oil, cognac oil, coriander oil, cumin oil, camphor oil, dill oil, estragon oil, *eucalyptus* oil, fennel oil, garlic oil, ginger oil, grapefruit oil, hop oil, lemon oil, lemongrass oil, nutmeg oil, mandarin oil, peppermint oil, orange oil, sage oil, star anise oil, terpentine oil, and resin; alcohol-based perfumes such as linalool, geraniol, nerol, citronellol, hydroxycitronellol, menthol, borneol, benzyl alcohol, anisic alcohol, β-phenethyl alcohol, n-octyl alcohol, n-octynol, n-nonyl alcohol, n-decyl alcohol, n-undecyl alcohol, n-undecylenic alcohol, duodecyl alcohol, tetrahydrolinalool, terpineol, isopulegol, borneol, isoborneol, farnesol, nerolidol, santalol, γ-phenylpropyl alcohol, cinnamic alcohol, methylphenylcarbinol, dimethylphenylcarbinol, dimethylbenzylcarbinol, β-phenylethyldimethylcarbinol, β-phenylethylmethylethylcarbinol, and phenoxyethyl alcohol; ether-based perfumes such as anisole, diphenyl oxide, dibenzyl ether, guaiacol, dimethyl hydroquinone, p-cresol methyl ether, anethole, eugenol, isoeugenol, methyleugenol, methyl isoeugenol, and benzyl isoeugenol; aldehyde-based perfumes such as n-butyraldehyde, isobutyraldehyde, hexylaldehyde, n-heptyl aldehyde, n-octyl aldehyde, n-nonylaldehyde, n-decyl aldehyde, n-undecylaldehyde, undecylenic aldehyde, methylnonylacetaldehyde, tridecylaldehyde, tetradecylaldehyde, hexadecylaldehyde, undecalactone, ethyl methylphenyl glycidate, γ-nonyllactone, citral, citronellal, hydroxycitronellal, benzaldehyde, p-tolylaldehyde, cuminaldehyde, phenylacetaldehyde, p-tolylacetaldehyde, phenylpropyl aldehyde, cinnamic aldehyde, α-amyl cinnamic aldehyde, p-isopropyl-α-methylhydrocinnamic aldehyde, salicylaldehyde, anisic aldehyde, heliotropin, vanillin, ethyl vanillin, and nonanal (pelargonic aldehyde); ketone-based perfumes such as methyl-n-amylketone, methyl-n-hexylketone, methyl-n-nonylketone, ethyl-n-amylketone, methylheptene, diacetyl, carvone, menthone, pulegone, piperitone, camphor, acetophenone, p-methylacetophenone, benzophenone, benzylideneacetone, methyl naphthyl ketone, ionone, methylionone, irone, jasmone, muscone, civetone, exaltone, γ-butyrolactone, and coumarin; ester-based perfumes such as formic acid ester, ester of acetic acid (for example, linalyl acetate), ester of propionic acid, ester of butyric acid, ester of valeric acid, ester of lactic acid, ester of hepthylic acid, ester of heptenecarboxylic acid, ester of octenecarboxylic acid, ester of lauric acid, ester of myristic acid, ester of benzoic acid, ester of phenylacetic acid, ester of cinnamic acid, ester of phthalic acid, ester of salicylic acid, ester of anisic acid, ester of anthranilic acid, ester of methylanthranilic acid, and ester of chrysanthemic acid; ethylene, acetylene, pinene, limonene, camphene, phellandrene, terpinolene, cadinene, caryophyllene, p-cymol, cineol, ambrettolide, Exaltolide, diphenylethane, benzoic acid, cinnamic acid, phenylacetic acid; and the like.

Examples of the malodorous substances include, for example, carboxylic acids such as nonanoic acid (for example, pelargonic acid), lactic acid, acetic acid, propionic acid, n-butyric acid, iso-butyric acid, n-valeric acid, iso-valeric acid, caproic acid, caprylic acid, capric acid, oleic acid, acrylic acid, and methacrylic acid; nitrogen compounds such as ammonia, methylamine, ethylamine, n-propylamine, n-butylamine, n-allylamine, dimethylamine, diethylamine, trimethylamine, triethylamine, ethylenediamine, pyridine, indole, and skatole; ethers such as ethyl ether and iso-propyl ether; sulfur compounds such as methyl mercaptan, ethyl mercaptan, n-propyl mercaptan, iso-propyl mercaptan, n-butyl mercaptan, t-butyl mercaptan, 2-propene-1-thiol, dimethyl sulfide, diethyl sulfide, di-n-propyl sulfide, di-iso-propyl sulfide, allyl sulfide, dimethyl disulfide, diethyl disulfide, ethyl methyl sulfide, and tetrahydrothiophene; aldehydes such as acetaldehyde, propionaldehyde, n-butyraldehyde, iso-butyraldehyde, furfural, benzaldehyde, and 2-nonenal; alcohols such as iso-propyl alcohol, n-butyl alcohol, iso-butyl alcohol, n-amyl alcohol, iso-amyl alcohol, n-hexyl alcohol, octyl alcohol, lauryl alcohol, allyl alcohol, benzyl alcohol, ethylene glycol monomethyl ether, ethylene glycol monomethyl ether acetate, ethylene glycol monoethyl ether, ethylene glycol monoethyl ether acetate, ethylene glycol monobutyl ether, ethylene glycol monobutyl ether acetate, diethylene glycol monomethyl ether, diethylene glycol monoethyl ether, and diethylene glycol monobutyl ether; ethers such as butyl acetate, iso-amyl acetate, benzyl acetate, ethyl acetate, methyl acrylate, ethyl acrylate, butyl acrylate, and dioctyl acrylate; halogen compounds such as trichloroethylene, tetrachloroethylene, paradichlorobenzene, and trichloroethane; phenols such as phenol, tricresol, and guaiacol; ketones such as acetone, methyl ethyl ketone, diethyl ketone, n-dipropyl ketone, n-dipropyl ketone, methyl n-butyl ketone, methyl iso-butyl ketone, and diacetyl; xylene, trimethylbenzene, ethyl benzene, iso-propyl benzene, styrene, naphthalene, isoprene, α-pinene, isophorone, and the like.

Examples of the (d) components to be stabilized include, for example, iodine, polyiodide ions (for example, triiodide ions), colorants or dyes; active ingredients of pharmaceuticals; polyphenol; flavonoid; alkaloid; acids; and physiologically functional substances such as vitamins; and the like.

Examples of the colorants or dyes are as described in the below (h) of (1.3).

Examples of the active ingredients of pharmaceuticals include, for example, corticoid, androgen, estrogen, progestogen, proton pump inhibitors, 5-HT1 antagonists, sympatholytic drugs, sympathomimetic drugs, anticholinergic agents, tranquilizers, antianxiety drugs, antidotes, analgesic drugs, calcium antagonists, antiemetic drugs, pituitary or hypothalamic hormones, antiparkinson drugs, antihistaminic drugs, angiotensin II antagonists, lidocaine, nitroglycerin, new quinolone antagonists, nonsteroidal antirheumatic drugs, steroids, cardiac glycosides, anticoagulants, benzodiazepine derivatives, benzimidazole derivatives, piperidine derivatives, piperazine derivatives, imidazole derivatives, triazole derivatives, organic nitrates, prostaglandins, oligonucleotide antisense drugs, acetylsalicylic acid, diclofenac sodium, ibuprofen, naproxen sodium, heparin, low-molecular-weight heparin, aspirin, coumazin, dextran, persantin, glibenclamide, antiviral drugs (for example, 3TC, AZT, ddC, loviride, indinavir, nelfinavir, tivirapine, ritonavir, squinavir, ddI and ISIS14803), lubeluzole, aptiganel, remacemide, glyceryl trinitrate, isosorbide dinitrate, isosorbide 5-mononitrate, pentaerythritol tetranitrate, amyl nitrate, prostaglandins, anticancer drugs (for example, ISIS3521 and ISIS5132), amitriptyline HCl, clomipramine HCl, fluoxetine, amoxapine, butriptyline HCl, amphotericin, econazole, flucytosine, miconazole nitrate, amoxicillin, cefaclor, cephalexin, flucloxacillin sodium, lincomycin HCl, clindamycin and the like. Examples of the polyphenols include, for example, catechin, tannin, oolong tea polyphenols, chlorogenic acid, cocoa mass polyphenols and the like. Examples of the flavonoids include, for example, anthocyanins, hesperidin, neohesperidin, rutin, naringin, quercetin, isoflavone, naringenin and the like. Examples of the alkaloid include, for example, capsaicin and the like. Examples of the acids include, for example, acetic acid, citric acid, malic acid, lactic acid, fumaric acid, tartaric acid, adipic acid and the like. Examples of the vitamins include, for example, vitamin A, vitamin $B_1$, vitamin $B_2$, vitamin $B_6$, vitamin C, vitamin D, vitamin E, nicotinic acid, nicotinic acid amide, pantothenic acid and the like.

Examples of the (e) sustainably released components include, for example, iodine, polyiodide ions (for example, triiodide ions), ethanol, microbicides, antimicrobial agents, insect proofing components, anti-molding components, odor components, deodorant components, cosmetic components, and physiologically functional substances (for example, active ingredients of pharmaceuticals; polyphenols; flavonoids; alkaloids; acids; vitamins). Examples of the microbicides and the antimicrobial agents are as described in the above (a) of (1.3). Examples of the insect proofing components are as described in the above (b) of (1.3). Examples of the anti-molding components are as described in the below (j) of (1.3). Examples of the odor components are as described in the above (c) of (1.3). Examples of the deodorant components are as described in the below (i) of (1.3). Examples of the cosmetic components are as described in the below (g) of (1.3). Examples of the active ingredients of pharmaceuticals; polyphenols; flavonoids; alkaloids; acids; and vitamins are as described in the above (d) of (1.3).

Examples of the (f) ultraviolet absorbing substances include, for example, nonyl phenol; cinnamic acid, cinnamic acids derivatives (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate (octyl parametoxycinnamate), 2-ethoxyethyl p-methoxycinnamate (cinoxate), cyclohexyl p-methoxycinnamate, ethyl α-cyano-β-phenylcinnamate, 2-ethylhexyl α-cyano-β-phenylcinnamate (Octocrylen), glyceryl mono-2-ethylhexanoyl-diparamethoxycinnamate, ferulic acid and derivatives thereof); benzoic acid, benzoic acid derivatives (for example, para-aminobenzoic acid, para-aminobenzoic acid monoglycerin ester, N,N-dipropoxy-paraminobenzoic acid ethyl ester, N,N-diethoxyparaminobenzoic acid ethyl ester, N,N-dimethylparaminobenzoic acid ethyl ester, N,N-dimethylparaminobenzoic acid butyl ester, and N,N-dimethylparaminobenzoic acid ethyl ester); salicylic acid, salicylic acid derivatives (for example, amyl salicylate, menthyl salicylate, homomethyl salicylate, octyl salicylate, phenyl salicylate, benzyl salicylate, and p-isopropanolphenyl salicylate); benzophenone, benzophenone derivatives; flavonoids (for example, anthocyanins, hesperidin, neohesperidin, rutin, naringin, quercetin, isoflavone and naringenin); 2-hydroxybenzotriazole derivative, 2-hydroxy-benzophenone derivatives (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, 2-hydroxy-4-n-dodecycloxybenzophenone), 3-(4'-methylbenzylidene)-d,l-camphor, 3-benzylidene-d,l-camphor, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, 2-(2'-hydroxy-3',5'-di-t-butylphenyl)-5-chlorobenzotriazole, 2-(2'-hydroxy-3'-t-butyl-5'-methylphenyl)-5-chlorobenzo triazole, 2-(2'-hydroxy-3',5'-di-t-butylphenyl)-5-chlorobenzotriazole, 2-(2'-hydroxy-3',5'-di-t-aminophenyl)benzotriazole, 2-(2'-hydroxy-3',5'-di-t-butylphenyl)benzotriazole, 2-(2'-hydroxy-5'-t-butylphenyl)benzotriazole, 2-(2'-hydroxy-5'-t-octylphenyl)benzotriazole, dibenzalazine, dianisoylmethane, 5-(3,3-dimethyl-2-norbornylidene)-3-pentan-2-one, 4-t-butylmethoxydibenzoylmethane, octyltriazone, urocanic acid, 1-(3,4-dimethoxyphenyl)-4,4-dimethyl-1,3-pentanedion, 2-ethylhexyl dimethoxybenzylidenedioxoimidazolidinepropionate, phenylbenzimidazolesulfonic acid, terephthalylidenedicamphorsulfonic acid, drometrizole trisiloxane, methyl anthranilate, urocanic acid derivative, hydantoin derivative, dibenzoylmethane derivative, 2,4-di-t-butylphenyl-3',5'-di-t-butyl-4'-hydroxybenzoate, phenyl salicylate, 2,4-di-t-butylphenyl-3',5'-di-t-butyl-4'-hydroxybenzoate, and ethyl-2-cyano-3,3-diphenyl acrylate.

Examples of the (g) cosmetic components include, for example, moisturizing components, whitening components, anti-inflammatory agents, cell activating agents, and antioxidants.

Examples of the moisturizing components include, for example, polyols and polymers thereof, such as chondroitin sulfate, hyaluronic acid, adenosin, glycerin, butylene glycol, hexylene glycol, 1,3-butylene glycol, propylene glycol, 1,2-hexanediol, 1,2-pentanediol, hexanetriol, dipropylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymer; organic acids (for example, citric acid, tartaric acid and lactic acid); glycol alkyl ethers such as diethylene glycol monoethyl ether (ethoxydiglycol), ethylene glycol monoethyl ether, ethylene glycol monobutyl ether, and diethylene glycol dibutyl ether; sugar alcohols such as sorbitol, xylitol, erythritol, mannitol, and maltitol; ethyl glucoside; glucosyl ethyl methacrylate polymer; amino acids such as betaine (trimethylglycine), proline, hydroxyproline, arginine, lysine, serine, glycine, alanine, phenylalanine, tyrosine, β-alanine, threonine, glutamic acid, glutamine, asparagine, aspartic acid, cysteine, cystine, methionine, leucine, isoleucine, valine, tryptophan, histidine, and taurine; proteins and peptides, such as degraded peptide of collagen, hydrolyzed collagen, hydroxypropylammonium chloride-hydrolyzed collagen, degraded peptide of elastin, degraded peptide of keratin, hydrolyzed keratin, degraded peptide of conchiolin, hydrolyzed conchiolin, degraded peptide of silk protein, hydrolyzed silk, lauroyl-hydrolyzed silk sodium, degraded peptide of soybean protein, degraded peptide of wheat protein, hydrolyzed wheat protein, degraded peptide of casein, acylated peptides, palmitoyl oligopeptides, palmitoyl pentapeptides, and palmitoyl tetrapeptide; ceramides such as natural type ceramide (types 1, 2, 3, 4, 5, and 6), hydroxyceramide, pseudo-ceramide, sphingoglycolipid, ceramide, and ceramide saccharide-containing extract; animal extracts and plant extracts, such as placenta extract liquid, elastin, collagen, aloe extract, hamamelis water, sponge gourd water, chamomile extract, Glycyrrhiza extract, comfrey extract, silk extract, *Rosa roxburghii* extract, yarrow extract, *eucalyptus* extract, and *Melilotus* extract; and the like.

Examples of the whitening components include, for example, arbutin, α-arbutin, tranexamic acid, ellagic acid, ascorbic acid, sodium ascorbate, ascorbic acid magnesium phosphate, disodium ascorbyl phosphate, ascorbic acid glucoside, ascorbyl monostearate, ascorbyl monopalmitate, ascorbyl dipalmitate, ascorbyl tetra-2-hexyldecanoate, disodium ascorbyl sulfate, sulfur, koj is acid, linoleic acid, linolenic acid, lactic acid, rucinol, chamomile extract, placenta extract, oil-soluble Glycyrrhiza extract, mulberry extract, peony extract, *Angelica acutiloba* extract, *Sanguisorba officinalis* extract, horse chestnut bark extract, *Bistorta officinalis* extract and the like.

Examples of the anti-inflammatory agents include, for example, ε-aminocaproic acid, allantoin, lysozyme chloride, guaiazulene, glycyrrhizinic acid and salts thereof, β-glycyrrhetinic acid, hydrocortisone and the like.

Examples of the cell activating agents include, for example, nucleic acid-related substances such as deoxyribonucleic acid and salts thereof, adenylic acid derivative and salts thereof, such as adenosine triphosphate and adenosine monophosphate, ribonucleic acid and salts thereof, cyclic AMP, cyclic GMP, flavin adenine dinucleotide, guanine, adenine, cytosine, thymine, xanthine, caffeine, and theophylline and salts thereof; extracts derived from animals (such as, mammalian, birds, shellfishes, insects, fishes, mollusks, and crustaceans) such as calf blood extract liquid, serum-removed protein extract, spleen extract, egg component derived from such as birds, cockscomb extract, shell extract, shellfish meat extract, royal jelly, silk protein and degraded products thereof or derivatives thereof, hemoglobin or degraded products thereof, lactoferrin or degraded products thereof, mollusk extract such as squid ink, and fish meat extract; extracts derived from microorganisms, for example, fermented metabolites of, such as, yeast extract, *Lactobacillus* extract, and *Bifidobacterium* extract; vitamins such as retinol and derivatives thereof (such as retinol palmitate and retinol acetate), retinal and derivatives thereof, dehydroretinal, carotenoids such as tretinoin and carotene, thiamines (thiamine hydrochloride and thiamine sulfate), riboflavine (such as riboflavin and riboflavin acetate), pyridoxines (such as pyridoxine hydrochloride and pyridoxine dioctanoate), flavin adenine dinucleotide, cyanocobalamin, folic acids, nicotine acids (such as nicotinic acid amide and benzyl nicotinate), and cholines; extracts derived from plants (or plant materials), for example, plants of Rubiaceae (for example, Madder, *Uncaria gambir* Roxb. (for example, gambir (leaves and young shoots of *Uncaria gambir* Roxb.))), red grape, *Mallotus japonicus*, *Akebia quinata*, hemp, morning glory, Azuki bean, asparagus, *Hydrangea macrophylla* var. *thunbergii*, *Gynostemma pentaphylla*, apricot, *Reynoutria japonica*, fig, *Ginkgo biloba*, *Bistorta officinalis*, *Cananga odorata*, *Asarum sieboldii*, and closely related species thereof (for example, *Asarum heteropoides* Fr. Schm. Var. *mandshuricum* (Maxim.) Litag) (for example, Asiasari Radix (roots with rhizome of *Asarum sieboldii* or *Asarum heteropoides* Fr. Schm. Var. *mandshuricum* (Maxim.) Litag), *Prunella vulgaris* ssp. *asiatica*, *Prunus mume*, *Arctostaphylos uva-ursi*, *Citrus unshiu*, *Eleutherococcus senticosus* (for example, Acanthopanacis Cortex (barks or roots of *Eleutherococcus senticosus*))), *Senna obtusifoia*, *Styphnolobium japonicum*, *Pisum sativum* L., barley, *Plantago asiatica*, *Abelmoschus esculentus*, *Inula britannica* ssp. *japonica* and plants belonging to the same genus (for example, Flos Inulae (flower head of *Inula britannica* ssp. *japonica* or plants belonging to the same genus)), *Panax ginseng*, *Juglans mandshurica* var. *sachalinensis*, *Ononis* (for example, *Ononis spinosa*), *Patrinia scabiosifolia*, *Fragaria*, Orange, Kaki Persimmon, *Glechoma hederacea* ssp. *grandis*, Cashew (for example, *Anacardium occidentale*), *Valeriana fauriei* Brig., *Trichosanthes cucumeroides*, *Chaenomeles sinensis*, guarana, *Chamaecrista nomame* (Siebold) H. Ohashi (for example, *Cassia nomame* (entire plant of *Chamaecrista nomame* (Siebold) H. Ohashi)), Bramble, kiwifruit, *Platycodon grandiflorus*, *Crysanthemums*, *Catalpa ovata*, *Rumex japonicus*, *Gymnema sylvestre*, cucumber, *Agrimonia pilosa* var. *japonica*, guava, *Lycium chinense*, Kudzu, plants of Lauraceae (for example, *Cinnamomum camphora*, *Cinnamomum cassia* Blume (for example, cinnamon (barks of *Cinnamomum cassia* Blume or other plants belonging to the same genus))), plants belonging to the genus *Sophora* (for example, *Sohora flavescens* (for example, Sophorae Radix (roots of *Sophora flavescens* Aiton), *Sophora subprostrala* CHUN et T. CHEN (for example, Sophorae subprostratae Radix (roots of *Sophora subprostrala* CHUN et T. CHEN)))), chestnut, mulberry (for example, *Morus alba* L.) or other plants belonging to the same genus (for example, Mori Cortex (root barks of mulberry or other plants belonging to the same genus))), Spatholobi Caulis (for example, *Millettia reticulata, Mucuna birdwoodiana*, etc.), Bay laurel, *Scutellaria baicalensis* Georgi (for example, *Scutellaria* root), *Rubus chingii*, pepper, coffee, *Scrophularia buergeriana, Jateorhiza columba* (for example, roots of *Jateorhiza columba*), Sugarcane, *Crataegus cuneata, Camellia Sasanqua, Zanthoxylum piperitum*, saffron, cherry tree, *Punica granatum, Aster tataricus*, Peony, *Acorus calamus*, Easter lily, *Equisetum arvense*, watermelon, *Stevia rebaudiana, Prunus salicina, Hedera helix*, European Pear, *Achillea millefolium, Juniperus communis*, horseradish, *Acorus gramineus, Oenanthe javanica, Polygala senega* and closely related species thereof (for example, *Polygala senega* var. *latifolia*), *Senna alexandrina, Swertia japonica*, plants belonging to the genus *Rheum* (for example, *Rheum palmatum, R. tanguticum, R. officanale, R. coreanum* and interspecific hybrids thereof (for example, Rhei Rhizoma (rhizome of *Rheum palmatum, R. tanguticum, R. officanale, R. coreanum* or inter specific hybrids thereof))), *Citrus aurantium*, tamarind, *Aralia elata*, dandelion, chicory, clove, *Schisandra chinensis*, Evening primrose, *Centella asiatica, Commelina communis, Polygonum multiflorum* Thunb. (for example, Polygoni multiflori Radix (massive roots of *Polygonum multiflorum* Thunb.)), *Tetragonia tetragonoides, Juglans regia* var. *orientis, Capsicum annuum*, Winter melon, *Angelica acutiloba* and closely related species thereof (for example, *Angelica acutiloba* (Siebold et Zucc.) Kitag. var. *sugiyamae* Hikino), *Eucommia ulmoides, Abelmoschus manihot, Capsella bursa-pastoris, Citrus natsudaidai, Ziziphus jujuba* and closely related species thereof (for example, Zizyphi Fructus (fruits of *Ziziphus jujuba* or closely related species)), *Nandina domestica, Picrasma quassioides*, garlic, carrot, *Achillea alpina*, pineapple, *Hibiscus*, papaya, basil, *Nelumbo nucifera, Hordeum vulgare* L. var. *nudum* Hook. f., *Coix lacryma-jobi* var. *ma-yuen* (for example, Coicis Semen (seeds of Pearl barley *Coix lacryma-jobi* var. *ma-yuen*, testa of which has been removed)), *Rosa rugosa* (for example, *Rosa rugosa* var. *pleva* (*Rosa rugosa* flower), plants belonging to the genus *Rosa* (for example, *Rosa multiflora*) (for example, Rosae Fructus (rose fruit)), *Iris domestica*, peanut, *Rabdosia japonica* Hara, *Trapa japonica*, pistachio, *Thujopsis dolabrata, Ampelopsis japonica, Eriobotrya japonica, Tussilago farfara, Rhus javanica, Eupatorium fortunei*, grape (for example, grape seeds), *Fagus crenata*, blueberry, Flor de Manita, *Saposhnikovia seseloides, Physalis alkekengi, Magnolia obovata, Chaenomeles speciosa* and closely related species thereof (for example, *Chaenomeles speciosa* or *Chaenomeles japonica* (for example, *Chaenomeles fructus* (fruits of *Chaenomeles speciosa* or *Chaenomeles japonica*)), hop, *Rosa rugosa* var. *pleva* flower bud, plants belonging to the genus *Ephedra* (for example, *Ephedra distachya, E. sinica, E. intermedia, E. equisetina* (for example, Ephedrae Herba (underground stems of *E. sinica, E. intermedia, E. equisetina*))), mango, *Bupleurum scorzonerifolium, Lythrum anceps, Cryptotaenia japonica*, mimosa, *Millettia reticulata* and closely related species thereof (for example, Spatholobi Caulis (Climbing stems) of such as *Millettia reticulata*), *Leonurus sibiricus* (for example, Leonuri Herba (entire plant of *Leonurus sibiricus*)), *Melilotus*, melon, *Magnolia quinquepeta*, peach, Mulukhiyah, *Alpinia oxyphylla* (for example, Alpiniae Fructus (fruits of *Alpinia oxyphylla*)), *Centaurea cyanus*, palm tree, *Alnus firma*, mistletoe, *Persicaria hydropiper, Phytolacca esculenta, Myrica rubra, Saxifraga stolonifera* Curtis, *Daphniphyllum macropodum, Artemisia indica* var. *maximowiczii, Angelica dahurica* (for example, Angelicae dahuricae Radix (roots of *Angelica dahurica*)), Rye, *Siraitia grosvenorii* (*Momordica grosvenorii* Swingle) (for example, Momordicae grosvenori Swingle fruit), orchid, longan, mung bean (for example, bean sprout of Mung bean), apple, lettuce, lemon, *Forsythia suspensa* Vahl and closely related species thereof (for example, *Forsythia viridissima* Lindley) (for example, Crude Drug Forsythiae Fructus (fruits of *Forsythia suspensa* Vahl or *Forsythia viridissima* Lindley)), rosemary, seaweed, soybean (for example, beans or bean sprout), Tea; extracts of mushrooms such as *Lentinula edodes, Agaricus blazei* Murill, *Ganoderma* (for example, *Ganoderma lucidum* (Leyss. ex. Fr.) Karst), *Polyporus umbellatus* Fries (for example, *Polyporus*), and *Poria cocos* (for example, *Poria*)); extract derived frommolasses; components derived from plants such as Hinokitiol and Cepharanthin; linoleic acid, α-linolenic acid, γ-linolenic acid, eicosapentaenoic acid and derivatives thereof; estradiol and derivatives thereof and salts thereof; organic acids such as glycolic acid, succinic acid, lactic acid and salicylic acid, and derivative thereof, and salts thereof; and the like.

Examples of the antioxidants include, for example, tocopherol, nordihydroguaiaretic acid, butylated hydroxyanisole, butylated hydroxytoluene, propyl gallate, octyl gallate, sodium hydrogen sulfite, erythorbic acid, sodium erythorbate, dilauryl thiodipropionate, tolylbiguanide, p-hydroxyanisole, ascorbyl palmitate, ascorbyl stearate and the like.

Examples of the (h) colorants or dyes include, for example, natural pigments for food such as *gardenia* pigment, safflower pigment, turmeric pigment, monascus pigment, carotene, annatto pigment, paprika pigment, *Dunaliella* pigment, palm oil pigment, Sandalwood red pigment, Beet Red, cochineal pigment, lac pigment, *Perilla* pigment, red cabbage pigment, red radish pigment, purple sweet potato pigment, purple corn pigment, grape pericarp pigment, grape juice pigment, blueberry pigment, elderberry pigment, chlorophyll, *Spirulina* pigment, cacao pigment, tamarind pigment, Kaki Persimmon pigment, kaoliang pigment, carbon powder pigment, madder pigment, boysenberry pigment, *Hibiscus* pigment, and onion pigment; synthetic pigments for food such as Yellow No. 4, Yellow No. 5, Red No. 2, Red No. 3, Red No. 40, Red No. 102, Red No. 104, Red No. 105, Red No. 106, Blue No. 1, and Blue No. 2; synthetic pigments for non-food such as Brown No. 201, Black No. 401, Violet No. 201, Violet No. 401, Blue No. 1, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 3, Red No. 104, Red No. 106, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230, Red No. 231, Red No. 232, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 4, Yellow No. 5, Yellow No. 201, Yellow No. 202, Yellow No. 203, Yellow No. 204, Yellow No. 205, Yellow No. 401, Yellow No. 402, Yellow No. 403-1, Yellow No. 404, Yellow No. 405, Yellow No. 406, Yellow No. 407; acid dyes such as Acid Red 14; basic dyes such as Arianor Sienna Brown, Arianor Madder Red, Arianor Steel Blue, Arianor Straw Yellow; nitro dyes such as HC Yellow 2, HC Yellow 5, HC Red 3, 4-hydroxypropylamino-3-nitrophenol, N,N'-bis(2-hydroxyethyl)-2-nitro-p-phenylenediamine, HC Blue 2, and Basic Blue 26; disperse dyes; surface-treated organic pigments; anthraquinones such as astaxanthin and alizarin; natural pigments and natural dyes, such as anthocyanidin, β-carotene, carotenal, capsanthin, chalcones, carthamin, quercetin, crocin, chlorophyll, curcumin, cochineal, shikonin, bixin, flavones, Betacyanin, henna, hemoglobin, lycopene, riboflavin, and rutin; oxidation dye intermediates and couplers, such as p-phenylenediamine, toluene-2,5-diamine, o-, m- or p-aminophenol, m-phenylenediamine, 5-amino-2-methylphenol, resorcin, 1-naphthol, and 2,6-diaminopyridine, and salts thereof; autooxidation-type dyes such as indoline; dihydroxyacetone; and the like.

Examples of the (i) deodorant components include, for example, iodine, polyiodide ions (for example, triiodide ions), extracts derived from plants such as *Wasabia* plants, *Brassica juncea, Forsythia* plants, *Osmanthus×fortunei, Paulownia tomentosa, Petasites japonicus, Farfugium japonicum*, lilac, *Diospyros kaki* Thunb., *Quercus serrata, Populus tremula* var. *sieboldii*, Fern, *Fraxinus lanuginosa* f. *serrata* and tea; extracts derived from mushrooms such as white mushroom; organic acids such as citric acid, malic acid, adipic acid, fumaric acid, lactic acid, gluconic acid, maleic acid and succinic acid; green tea flavonoids, lauryl methacrylate, geranyl crotonate, acetophenone myristate, paramethylacetophenone benzaldehyde, benzyl acetate, benzyl propionate, amylcinnamic aldehyde, anisic aldehyde, diphenyl oxide, methyl benzoate, ethyl benzoate, methyl phenylacetate, ethyl phenylacetate, neoline, safrole, cedarwood oil, cedar oil, citronella oil, lavandin oil, Petitgrain oil, lemon grass oil, 3,4-hexanedione, 2,3-heptanedione, 5-methyl-2,3-hexanedione, 2,3-pentanedione, 3-methylcyclopentane-1,2-dione, 3,4-dimethylcyclopentane-1,2-dione, 3,5-dimethylcyclopentane-1,2-dione, cyclohexane-1,2-dione, diethyl malonate, diethyl tartrate, diethyl 2-methyl-3-buten-2-ol mandelate, copper chlorophyll and the like.

Examples of the (j) anti-molding components include, for example, iodine, polyiodide ions (for example, triiodide ions), thymol, hinokitiol, d-limonene, thiabendazole, methyl benzoimidazolyl carbamate, α-bromocinnamic aldehyde, parachlorometaxylenol, ortho-phenylphenol, N-(fluorodichloromethylthio)-phthalimide, and N-dichlorofluoromethylthio-N',N'-dimethyl-N-phenylsulfamide; organoiodine compounds such as 3-iodo-2-propynylbutyl carbamate, 3-bromo-2,3-diiodo-2-propenylethyl carbonate, 2,3,3-triiodoallyl alcohol, iodopropargyl alcohol, 3-iodopropargyl-4-chlorophenyloxy methyl ether, diiodomethyl-p-tolylsulfone; and the like.

(2. Method for Producing Amylose-Containing Rayon Fibers)

(2.1) Aqueous Alkaline Solution of Amylose

In the production method of the present invention, an aqueous alkaline solution of amylase is produced. The amount of the amylose in the alkaline solution is preferably about 1% by weight or more, more preferably about 5% by weight or more, further preferably about 10% by weight or more, and most preferably about 15% by weight or more. The amount of the amylose in the alkaline solution is preferably about 60% by weight or less, more preferably about 50% by weight or less, further preferably about 40% by weight or less, still more preferably about 30% by weight or less, especially preferably about 25% by weight or less, and most preferably about 20% by weight or less. When the concentration of amylase is too low, the amount of water added to viscose increases, and thus spinnability may sometimes deteriorate. When the concentration of amylose is too high, it may become difficult to uniformly mix amylose within viscose.

Any alkaline base agent used in the production of conventional viscose can be used as an alkaline base agent. The alkaline base agent is any substance which exhibits alkalinity when dissolved in water. Examples of the alkaline base agent include sodium hydroxide, potassium hydroxide, sodium phosphate, potassium phosphate, sodium carbonate and potassium carbonate. The alkaline base agent is preferably sodium hydroxide or potassium hydroxide. It is noted that, actually, the alkaline base agent is present in an aqueous solution in a state of dissociated ions, however, in the present specification, it is described that the alkaline base agent is present in an aqueous solution, including such dissociated ionic state. For example, sodium hydroxide is dissociated into hydroxide ion and sodium ion in an aqueous solution, but it is described that sodium hydroxide is present in the aqueous solution.

The alkaline base agent can be used in an alkaline liquid in any concentration. The concentration of the alkaline base agent is preferably about 0.25 N or more and about 10 N or less, and more preferably about 0.5 N or more and about 2 N or less. When the concentration of the alkaline base agent is too low, amylose may not be dissolved. When the concentration of the alkaline base agent is too high, the amylose solution may cause a chemical change such as browning.

The aqueous alkaline solution of amylose can be prepared by dispersing an amylose powder in water, and adding an alkaline to it, followed by stirring. Amylose has a property such that it is quite easily to be crystallized, and thus the amylose molecules are strongly bound in the state of amylose powder. Therefore, if amylose is mixed with viscose in the powder state, it is liable that amylose may not exert the clathrate action sufficiently when it becomes amylose-containing rayon. In the present invention, therefore, it is important to sufficiently dissolve amylose in the aqueous alkaline solution in advance. When the amylose powder is dissolved in the aqueous alkaline solution, the bonds between the amylose molecules are loosened and thus the amylose molecules have a random structure, and thus enabling amylose to sufficiently exert the clathrate action when it becomes amylose-containing rayon.

(2.2) Viscose

In the present invention, conventional viscose known in the art can be used. It is preferred that the concentration is appropriately adjusted, considering the dilution due to mixing with the aqueous alkaline solution of amylose.

(2.3) Mixing of Aqueous Alkaline Solution of Amylase with Viscose

The above aqueous alkaline solution of amylose and viscose can be mixed by any method known in the art. There is no particular limitation on the mixing method. A device for adding the aqueous alkaline solution of amylose in the viscose and mixing them may be an injection or homomixer type device. The timing of the addition and mixing may be arbitrary. For example, the addition and mixing may be carried out after degassing the viscose, or may be carried out before degassing, followed by degassing.

The mixing ratio of the aqueous alkaline solution of amylose to the viscose can be appropriately set. When the total weight of the cellulose component and amylose in the obtained mixed liquid is assumed to be 100% by weight, the amount of the amylose is preferably about 5% by weight or more, more preferably about 10% by weight or more, still more preferably about 15% by weight or more, and most preferably about 20% by weight or more. When the total weight of the cellulose component and amylose in the obtained mixed liquid is assumed to be 100% by weight, the amount of the amylose is preferably about 70% by weight or less, more preferably about 60% by weight or less, still more preferably about 50% by weight or less, and most preferably about 40% by weight or less. The larger the amount of the amylose relative to those of the cellulose component, the better since the clathrate action enhances. However, too much amylose may sometimes cause deterioration of filterability, exertion of an adverse influence on spinnability, and a decrease in fiber strength.

(2.4) Spinning

Amylose-containing rayon tow can be obtained by spinning an amylose-containing viscose solution using a conventionally known method. After the spinning, the rayon is in the form of tow, and when the tow is refined by a conventionally known method, as it is in a state of the tow or after the tow is cut into any fiber length, functional rayon fibers are obtained. In some cases, the amylose-containing rayon tow may be cut at the time of post-processing.

(2.5) Heating and Cooling Treatment

If the obtained amylose-containing rayon fibers are subjected to, for example, a heating step and a cooling step in a solvent after producing the fibers, the ability of amylase to form a clathrate may be improved.

Examples of the solvent to be used include water, methanol, ethanol, propanol, butanol, isopropanol, acetone, acetonitrile, propionitrile, tetrahydrofuran, 1,4-dioxane, methyl isobutyl ketone, methyl ethyl ketone, γ-butyrolactone, propylene carbonate, sulfolane, nitromethane, N,N-dimethylformamide, N-methylacetamide, dimethyl sulfoxide, dimethyl sulfone, N-methylpyrrolidone, benzene, toluene, xylene, methylene chloride, chloroform and dichloroethane.

A solution prepared by mixing an organic solvent with water is preferred. Examples of the organic solvents include methanol, ethanol, propanol, butanol, isopropanol, acetone, acetonitrile, propionitrile, tetrahydrofuran, 1,4-dioxane, methyl isobutyl ketone, methyl ethyl ketone, γ-butyrolactone, propylene carbonate, sulfolane, nitromethane, N,N-dimethylformamide, N-methylacetamide, dimethyl sulfoxide, dimethyl sulfone, N-methylpyrrolidone, benzene, toluene, xylene, methylene chloride, chloroform, and dichloroethane.

The amount of the organic solvent added to water can be about 0.5 parts by volume or more, about 1 part by volume or more, about 2 parts by volume or more, about 4 parts by volume or more, or the like, based on 10 parts by volume of water. The organic solvent can be added to water until the solubility of the organic solvent to water reaches the upper limit. The amount of the organic solvent added to water can be, for example, about 100 parts by volume or less, about 95 parts by volume or less, about 90 parts by volume or less, about 80 parts by volume or less, about 60 parts by volume or less, about 40 parts by volume or less, about 20 parts by volume or less, or the like, based on 10 parts by volume of water.

There is no particular limitation on the heating temperature and the heating time. The heating temperature can be, for example, about 80° C. or higher, about 90° C. or higher, about 100° C. or higher, about 110° C. or higher, about 120° C. or higher, about 130° C. or higher, or the like. As long as no particular adverse effect is exerted, except for a change in the state of amylose, the temperature may be any temperature. The heating temperature can be, for example, about 200° C. or lower, about 180° C. or lower, about 160° C. or lower, about 140° C. or lower, or the like. The heating time can be, for example, about 5 minutes or more, about 10 minutes or more, about 20 minutes or more, about 30 minutes or more, about 40 minutes or more, about 50 minutes or more, about 60 minutes (1 hour) or more, about 2 hours or more, about 3 hours or more, about 4 hours or more, about 5 hours or more, about 6 hours or more, about 8 hours or more, about 12 hours or more, about 24 hours or more, or the like. The heating time can be about 1 month or less, about 1 week or less, about 3 days or less, about 2 days or less, about 1 day (24 hours) or less, about 18 hours or less, about 16 hours or less, about 14 hours or less, about 12 hours or less, about 10 hours or less, about 8 hours or less, about 6 hours or less, about 5 hours or less, about 4 hours or less, about 3 hours or less, about 2 hours or less, about 1 hour or less, about 30 minutes or less, about 20 minutes or less, about 10 minutes or less, or the like.

After heating, the amylose-containing rayon is cooled to a predetermined temperature (for example, room temperature). The predetermined temperature can be, for example, about 10° C. or higher, about 15° C. or higher, about 20° C. or higher, about 25° C. or higher, or the like. The predetermined temperature can be, for example, about 30° C. or lower, about 25° C. or lower, about 20° C. or lower, or the like. In a certain embodiment, the cooling step from the heating temperature to the predetermined temperature may be carried out by leaving the amylase-containing rayon standing to cool. That is, the time required to cooling varies depending on the ambient temperature of the amylose-containing rayon. In another certain embodiment, the period of time for cooling from the heating temperature to the predetermined temperature is preferably a time as short as possible. In this embodiment, the time required to cooling can be, for example, about 10 seconds or more, about 20 seconds or more, about 30 seconds or more, about 1 minute or more, about 5 minutes or more, or the like. In the embodiment which prefers cooling in a short time, the time required to cooling can be, for example, about 5 hours or less, about 4 hours or less, about 3 hours or less, about 2 hours or less, about 1 hour or less, or the like.

The heating step and the cooling step may be carried out after spinning the amylose-containing rayon and before drying the same, or may be carried out after spinning the amylose-containing rayon and after drying the same. The amylose-containing rayon fibers can be dried by a conventional method, if necessary, after the heating and cooling treatment.

(2.6) Alkali Treatment

The obtained amylose-containing rayon fibers may have improved ability of amylase to form a clathrate by, for example, subjecting to an alkaline treatment, followed by neutralization.

An alkaline base agent that can be used in the alkaline treatment can be any alkaline base agent. Examples of the alkaline base agent include sodium hydroxide, potassium hydroxide, sodium phosphate, potassium phosphate, sodium carbonate, potassium carbonate and calcium carbonate. An alkaline base agent is preferably sodiumhydroxide, potassium hydroxide, sodium phosphate or sodium carbonate. Furthermore, the alkaline base agent can be a mixture of these alkalis.

An acid that can be used in the neutralization treatment can be any acid. Examples of the acids include inorganic acids such as hydrochloric acid, sulfuric acid, nitric acid, phosphoric acid, carbonic acid, hydrogencarbonic acid and perchloric acid; and organic acids such as acetic acid, propionic acid, lactic acid, maleic acid, fumaric acid, tartaric acid, malic acid, citric acid and ascorbic acid. A mixture of these acids may also be used.

The alkaline treatment and the acid treatment are preferably carried out by immersing the amylose-containing rayon in an aqueous alkaline solution bath or an aqueous acid solution bath, or may be carried out by any other method such as spraying or stamping in some cases.

The concentration of the aqueous alkaline solution varies depending on the kind and concentration of the alkaline base agent. The concentration of the aqueous alkaline solution is preferably about $1\times10^{-5}$ N or more, more preferably about $1\times10^{-4}$ N or more, much more preferably about $1\times10^{-3}$ N or more, still more preferably about $1\times10^{-2}$ N or more, and still further preferably about $1\times10^{-1}$ N or more. The concentration of the aqueous alkaline solution is preferably about 20 N or less, more preferably about 10 N or less, much more preferably about 5 N or less, and still more preferably about 1 N or less.

The concentration of the aqueous acid solution varies depending on the kind and concentration of the acid. The concentration of the aqueous acid solution is preferably about $1\times10^{-5}$ N or more, more preferably about $1\times10^{-4}$ N or more, much more preferably about $1\times10^{-3}$ N or more, still more preferably about $1\times10^{-2}$ N or more, and still further preferably about $1\times10^{-1}$ N or more. The concentration of the aqueous acid solution is preferably about 20 N or less, more preferably about 10 N or less, much more preferably about 5 N or less, and still more preferably about 1 N or less.

There is no particular limitation on the temperature of the aqueous alkaline solution or aqueous acid solution at the time of alkaline treatment and acid treatment. The temperature of the aqueous alkaline solution or aqueous acid solution can be, for example, about 120° C. or lower, about 110° C. or lower, about 100° C. or lower, about 90° C. or lower, about 80° C. or lower, about 70° C. or lower, about 60° C. or lower, about 50° C. or lower, about 40° C. or lower, or the like. The temperature of the aqueous alkaline solution or aqueous acid solution can be, for example, about 0° C. or higher, about 5° C. or higher, about 10° C. or higher, about 15° C. or higher, about 20° C. or higher, about 25° C. or higher, about 30° C. or higher, about 35° C. or higher, about 40° C. or higher, about 50° C. or higher, or the like. The heating time of the alkaline treatment and acid treatment can be, for example, about 10 minutes or more, about 20 minutes or more, about 30 minutes or more, about 40 minutes or more, about 50 minutes or more, about 60 minutes (1 hour) or more, about 2 hours or more, about 3 hours or more, about 4 hours or more, about 5 hours or more, about 6 hours or more, about 8 hours or more, about 12 hours or more, about 24 hours or more, or the like, respectively. The heating time of the alkaline treatment and acid treatment can be, for example, about 1 month or less, about 1 week or less, about 3 days or less, about 2 days or less, about 1 day (24 hours) or less, about 18 hours or less, about 16 hours or less, about 14 hours or less, about 12 hours or less, about 10 hours or less, about 8 hours or less, about 6 hours or less, about 5 hours or less, about 4 hours or less, about 3 hours or less, about 2 hours or less, about 1 hours or less, about 30 minutes or less, about 20 minutes or less, about 10 minutes or less, or the like.

The alkaline treatment may be carried out after spinning the amylose-containing rayon and before drying the same, or may be carried out after spinning the amylose-containing rayon and after drying the same. The amylose-containing rayon fibers can be dried by a conventional method, if necessary, after the alkaline treatment.

The functional rayon fibers having sufficient clathrate function can be obtained as described above. It is noted that the rayon fibers mentioned in the present invention is used in the meaning including not only viscose rayon fibers, but also regenerated cellulose fibers such as high strength rayon fibers, ultra-high strength rayon fibers, polynosic fibers, HWM (high wet modulus) fibers and cupra fibers.

(3. Amylose-Containing Rayon Fibers)

In the amylose-containing rayon fibers of the present invention, amylose is dispersed and retained in the rayon fibers. Herein, it is considered that amylose is nearly uniformly dispersed and retained in the rayon fibers.

The amount of the amylose dispersed and retained in the rayon fibers can be set arbitrarily by changing the mixing ratio of cellulose to amylase in the viscose in the production of the amylose-containing rayon fibers. The amount of the amylose dispersed and retained in the rayon fibers is preferably about 1% by weight or more, more preferably about 5% by weight or more, and still more preferably about 10% by weight or more, when the total amount of the cellulose and the amylose in the rayon fibers is assumed to be 100% by weight. The amount of the amylose dispersed and retained in the rayon fibers is preferably about 60% by weight or less, more preferably about 50% by weight or less, much more preferably about 40% by weight or less, still more preferably about 30% by weight or less, and still further preferably about 20% by weight or less, when the total amount of the cellulose and amylose in the rayon fibers is assumed to be 100% by weight. When the amount of the amylose dispersed and retained in the rayon fibers is too small, the objective effect may not be sufficiently obtained. When the amount of the amylose dispersed and retained in the rayon fibers is too large, the viscosity of the viscose increases, and thus it may sometimes become difficult to stably produce the rayon fibers, and physical properties such as strength and elongation degree of the rayon fibers may sometimes deteriorate.

It is preferred that the amylose-containing rayon fibers are subjected to at least one of the heating and cooling treatment as described in the above (2.5) and the alkaline treatment as described in the above (2.6). The reason is that the ability of amylase to form a clathrate can be improved by subjecting to the heating and cooling treatment or the alkaline treatment.

In a specific embodiment, the amylose-containing rayon of the present invention does not contain a quaternary ammonium salt compound and have not been treated with a quaternary ammonium salt compound.

The amylose-containing rayon of the present invention is either in the state of not making clathrate with guest substance or in the state of making clathrate with a guest substance. When the amylose-containing rayon not making clathrate with guest substance is contacted with a substance capable of being making a clathrate with amylose, it makes a clathrate with the substance. The amylose-containing rayon in the state of a clathrate with a guest substance can release the guest substance by a change in heat, moisture, or the like, similarly to a conventional clathrate compound.

(3.1) Amylose is not Substantially Eluted by Washing

In the amylose-containing rayon fibers of the present invention, amylose is not substantially eluted by washing. As used in the present specification, the expression "amylose is not substantially eluted by washing" means that the amount of the amylose eluted by washing accounts for 10% by weight or less of the entire amylose contained in the amylose-containing rayon fibers. It is preferred that the ease of elution of amylose from the amylose-containing rayon fibers is determined by the following conditions: the amylose-containing rayon fibers are immersed in a 40-fold amount of a washing solution (an aqueous 0.75 mg/mL detergent solution; as a detergent for example, TOP manufactured by Lion Corporation (which contains 24% of a surfactant (sodium alpha-sulfo fatty acid ester, fatty acid sodium salt, polyoxyethylenealkyl ether), and as other components, an alkaline agent (carbonate), a dissolution accelerator, an enzyme, a fluorescent whitening agent and a bleaching agent)) for 3 hours and then subjected to centrifugal filtration at 12,000×g for 4 minutes using a filter, and then the amount of the amylose in the obtained filtrate is measured and the proportion of the amylose eluted is calculated.

The elution amount of amylase under these conditions is preferably about 10% by weight or less, more preferably about 8% by weight or less, and still more preferably about 5% by weight or less, particularly preferably about 3% by weight or less, and most preferably about 1% by weight or less, based the entire amylose contained in the amylose-containing rayon fibers. The elution amount is remarkably preferably about 0.5% by weight or less, about 0.4% by weight or less, about 0.3% by weight or less, about 0.2% by weight or less, about 0.1% by weight or less, about 0.05% by weight or less, or about 0.01% by weight or less.

(3.2) Ability of Making Clathrate with Guest Substance

In the present specification, the expression "having the ability of making a clathrate with a guest substance" means that an amylose is in a state where the amylose can make clathrate including a guest substance. The clathrate includes, in addition to intramolecular clathrate, intermolecular clathrate. The intramolecular clathrate means a phenomenon in which a guest substance is included in one molecule of amylose. The intermolecular clathrate means a phenomenon in which a guest substance is included between a plurality of amylose molecules, or between an amylose molecule and a cellulose molecule.

There are three types of crystal forms called type A, type B and type V in natural amylose and synthetic amylose. The crystal form varies depending on a difference in the kinds of plants, extraction solvents, precipitants or the like when extracting and purifying it from a natural starch. The type A amylose is obtained from a starch of grains such as wheat and corn. The type B amylose is obtained from a starch of tubers and roots such as potato and sweet potato. Any of type A amylose and type B amylose takes a structure in which α-1, 4-glucan chains are arranged in parallel and form double helices. In contrast, the type V amylose is obtained by adding a precipitant such as ethanol or butanol to a natural starch. The type V amylose takes a structure in which an α-1,4-glucan chain forms a single helice. When amylose is in a powder state, the type A amylose and the type B amylose have no ability to form an intramolecular clathrate, while the type V amylose has ability to form an intramolecular clathrate. On the other hand, it is considered that the type A amylose and the type B amylose have ability to form a intermolecular clathrate, while the type V amylose has both abilities to form a intramolecular clathrate and intermolecular clathrate, when amylose is contained in the rayon fibers.

Furthermore, amorphous amylose can also exhibit ability to form a clathrate. It is considered that this type of amylose takes a specific structure when a guest substance is present, and thus converting into the state capable of exerting the clathrate action.

The crystal form of amylose can be determined by a known method in the art. For example, it can be determined in accordance with the description of International Publication No. WO 2006/082968 pamphlet, using X-ray diffraction. Simply, it is possible to determine whether or not amylose is in the state capable of exerting the clathrate action by testing whether or not amylose makes clathrate with nonyl phenol. The amylose in the state capable of exerting the clathrate action is also referred to as functionable amylose.

(3.3) Measurement of Ability of Amylase to Form a Clathrate

The ability of the amylose-containing rayon of the present invention to form a clathrate is measured by using nonyl phenol as a guest substance.

Amylose-containing rayon fibers (50 mg) are impregnated with nonyl phenol by immersing amylose-containing rayon fibers in 3 mL of an aqueous 50% methanol solution containing nonyl phenol in a concentration of 100 ppm at 25° C. for 3 hours. The obtained amylose-containing rayon fibers are packed in a column and washed twice with 5 mL of an aqueous 10% methanol solution. The nonyl phenol in clathrate is eluted twice with 5 mL of methanol and the eluate is collectively recovered. The amount of the nonyl phenol in the eluate is quantitatively determined by HPLC, and the amount of the nonyl phenol in clathrate is determined. The ability of the amylose-containing rayon to form a clathrate is defined by the following equation.

$$\text{ability of amylose-containing rayon fibers to form a clathrate (\%)} = 100 \times \{(\text{clathrate amount of nonyl phenol (mg)})/0.3 \text{ (mg)}\} \quad \text{[Equation 1]}$$

The conditions of liquid chromatography are, for example, as follows.

TSKgel ODS-100Z (manufactured by TOSOH CORPORATION) is used as a column and a UV detector SPD-6A (manufactured by Shimadzu Corporation) is used as a detector, and LC-6A (manufactured by Shimadzu Corporation) is used as a feed pump. Analysis is carried out by maintaining the column temperature at 40° C. using 80% methanol as an eluant at a flow rate of 1.0 mL/minute.

If control rayon fibers which are the same as amylose-containing rayon fibers except for containing no amylase is washed with an aqueous 10% methanol solution, nonyl phenol adsorbed to the control rayon fibers is entirely eluted. Thus, when control rayon fibers can be prepared, the ability to form a clathrate can also be determined by the following method.

50 mg of Amylose-containing rayon fibers and Control rayon fibers containing no amylose are respectively impregnated with nonyl phenol by immersing in 3 mL of an aqueous 50% methanol solution containing nonyl phenol in a concentration of 100 ppm at 25° C. for 3 hours. The concentration of nonyl phenol in the aqueous solution is measured before and after immersion using liquid chromatography. From a decrease in an amount of nonyl phenol before and after immersion of the rayon fibers, the adsorption ratio (%) of nonyl phenol is determined by the following equation.

$$\text{Adsorption ratio of nonyl phenol to rayon (\%)} = \quad \text{[Equation 2]}$$
$$100 - (\text{recovery ratio of nonyl phenol (\%)})$$

$$\text{Recovery ratio of nonyl phenol (\%)} =$$
$$100 \times \left\{ \frac{(\text{concentration of nonyl phenol after immersion of rayon})}{(\text{concentration of nonyl phenol before immersion of rayon})} \right\}$$

The ability of the amylose-containing rayon to form a clathrate is defined by the following equation.

$$\text{ability of amylose-containing} \quad \text{[Equation 3]}$$
$$\text{rayon fibers to form a clathrate (\%)} =$$

nonyl phenol adsorption ratio of amylose-containing rayon fibers (%) − nonyl phenol adsorption ratio of control rayon fibers (%)

Since amylose can include but cannot adsorb nonyl phenol, the ability of amylase to form a clathrate can be calculated by this equation.

(4. Mode of Use of Amylose-Containing Rayon of the Present Invention)

The amylose-containing rayon fibers of the present invention can be used in various modes. The amylose-containing rayon fibers of the present invention can be suitably used as they are in a cotton form, or used as a yarn alone or in combination with other fibers, or used as fabrics such as a knit, textile and a nonwoven fabric (including a paper-like wet nonwoven fabric), or used as clothes, curtains, beddings, shoji paper, wall paper, hats, carpets, cover materials for sofas, and other deodorizing products. The amylose-containing rayon fibers of the present invention can be used for various secondary processed articles similar to conventional rayon fibers. Such secondary processed articles include cotton, yarn, nonwoven fabric, cloth, paper and the like. A method of producing these secondary processed articles from the amylose-containing rayon fibers is known in the art. For example, when paper is produced from the amylose-containing rayon fibers, the amylose-containing rayon fibers that are cut into short fibers are used alone or in combination with a conventional raw material for paper, followed by paper making, whereby paper can be produced form the amylose-containing rayon fibers. The amylose-containing rayon fibers of the present invention can be used in further highly processed articles made from these secondary processed articles such as clothing, fabric, filters, processed articles for cosmetic, medical supplies, daily articles, packages and hygienic material for such as sanitary goods. Fabric means a product using a cloth, a woven fabric or the like. In the interior industry, fabric is often used in a slighter broader sense than a generic term of a cloth and a woven fabric, and refers any articles using a cloth, such as, curtains, table clothes, cover clothes for chairs and sofas, cushions and bedcovers, and also includes a wall covering material of a cloth.

(5. Purpose of Use of the Present Invention)

Purpose of use of the amylose-containing rayon fibers of the present invention can be roughly classified into the following two purposes: (1) a method in which the amylose-containing rayon fibers are used as they are without allowing them to make a clathrate including a guest substance, and (2) a method in which the amylose-containing rayon fibers are used in the state of clathrate including a guest substance.

(5.1) Method of Using the Amylose-Containing Rayon Fibers as they are without Allowing them to Make a Clathrate Including a Guest Substance In the method in which the amylose-containing rayon fibers are used as they are without allowing them to make a clathrate including a guest substance, the function making clathrate with various substances of amylose can be used for the purposes of (A) concentrating (recovery), (B) removal, (C) purification, and the like. The respective purposes of use will be described below.

(A) Purpose of Concentrating (Recovery)

The term "concentrating" means that a target substance existing in a dilute state is collected and the concentration thereof is increased. Examples of the target substance include iodine, polyiodide ions and the like. Specific examples of products for the purpose of concentrating include filters and columns for recovery of these target substances (for example, filters and columns for recovery of iodine). There is also a batch-type method of use in which the amylose-containing rayon fibers are placed as they are in a container or the like containing mixtures and, after adsorption (clathrate) of the objective substance, the amylose-containing rayon fibers are recovered and the objective substance is eluted and recovered therefrom.

(B) Purpose of Removal

The term "removal" means that a target substance or a contaminant contaminated in a product is collected and removed. Examples of the target substance and the contaminant to be removed include iodine, polyiodide ions and the like. Specific examples of products for the purpose of removal include a filter for removing contaminants, a filter for removing exhaust gas component, a filter for purifying water, a filter for cleaning air, a mask, a cleaning product, a personal washing product and the like. There is also a method for use in which the amylose-containing rayon fibers are placed as they are in a container or the like containing the product and a foreign substance is removed.

(C) Purpose of Purification

The term "purification" means that a specific substance is purified from a mixture to obtain a pure substance. Examples of the substance to be purified include iodine, polyiodide ions and the like. Specific examples of products for the purpose of purification include filters and columns for recovering the target substance (for example, filters and columns for recovering iodine). There is also a batch-type method of use in which the amylose-containing rayon fibers are placed as they are in a container containing mixtures and, after adsorption (clathrate) of the objective substance, the amylose-containing rayon fibers are recovered and the objective substance is eluted and recovered therefrom.

(5.2) Method Using in a State where Guest Substance is in a Clathrate

In the method using in the state where a guest substance is in a clathrate, the amylose-containing rayon fibers can be used for purposes by devising various guest substances, such as (D) microbiocidal or antimicrobial purpose, (E) insect proofing or anti-molding purpose, (F) aromatizing or deodorizing purpose, (G) stabilization, (H) sustained release, (I) ultraviolet protection, (J) imparting of cosmetic functions and (K) imparting of medical functions. The respective use purposes will be described below.

(D) Microbiocidal or Antimicrobial Purpose

The term "microbicide" refers to killing microorganisms. The term "antimicrobe" refers to suppress or inhibit proliferation of microorganisms. The microorganisms refer to organisms of a microscopic size. Examples of the microorganisms include bacteria, fungi (for example, yeast), protozoa, viruses and the like. Products for microbiocidal or antimicrobial purpose are products for the purpose of killing or inhibiting microorganisms from proliferation on the surface of or inside the products.

Examples of a guest substance to be clathrate with the amylose-containing rayon fibers for these purposes are as described in the above (a) of (1.3). For example, when the guest substance is iodine or polyiodide ions, the amylose-containing rayon fibers or a product combined therewith (for example, fabrics such as nonwoven fabric, knit fabric and textile) contains iodine or polyiodide ions in the total of preferably about 0.01% by weight or more, more preferably about 0.02% by weight or more, and still more preferably about 0.03% by weight or more. The total weight of iodine and polyiodide ions can be, for example, about 0.04% by weight or more, about 0.06% by weight or more, about 0.08% by weight or more, about 0.10% by weight or more, or the like. The total weight of iodine or polyiodide ions can be arbitrary weight as long as they can be included in a clathrate, but preferably about 15% by weight or less, more preferably about 10% by weight or less, still more preferably about 5% by weight or less, still further preferably about 3% by weight or less, and most preferable about 1% by weight or less.

Specific examples of products for microbiocidal or antimicrobial purpose include iodine-containing masks, iodine-containing work uniforms, iodine-containing towels, hygienic goods (masks, gloves, aprons, hats and caps, pillow cases, seat head covers, wet tissue, kitchen clothes, shoe inserts, shoe deodorants, clothes covers, and the like), building materials inside walls, wallpapers, gauze, bandages, cotton swabs, beddings (pillow cases, sheets, futon covers, cotton in pillows or futons, and the like), interior products (curtains, shoji, sofa covers, doormats, cotton in cushions, and the like), and kitchen or bath or toilet products (wet tissue, toilet seat covers, toilet mats, bath mats, kitchen mats, and the like).

(E) Purpose of Insect Proofing or Anti-Molding

The term "insect proofing" means to repel insects and prevent insects from being attached. The term "anti-molding" means to inhibit proliferation of mildew. Examples of a guest substance to be made clathrate with the amylose-containing rayon fibers for this purpose include insecticides and anti-molding agents. Examples of the insecticide are described in the above (b) of (1.3). Examples of the anti-molding agents are as described in the above (j) of (1.3).

Specific examples of products include insect proofing sheets, insect proofing mats, insect proofing curtains, insect proofing clothes, anti-molding sheets, anti-molding mats, anti-molding curtains, anti-molding clothing and the like.

(F) Purpose of Aromatizing or Deodorizing

The term "aromatizing" means to confer flavor by adding flavor components (perfumes). The term "deodorizing" means to remove odor.

Examples of a guest substance to be made clathrate with the amylose-containing rayon fibers for the aromatizing purpose are as described in the above (c) of (1.3).

Examples of a guest substance to be made clathrate with the amylose-containing rayon fibers for the deodorizing purpose include deodorizing agents. Examples of the deodorizing agent are described in the above (i) of (1.3).

Specific examples of products for aromatizing and deodorizing purposes include clothing, hygienic goods (for example, masks, gloves, aprons, hats and caps, pillow cases, seat head covers, wet tissue, kitchen clothes, shoe inserts, shoe deodorants, clothes covers and the like), building materials inside walls, wall papers, gauze, bandages, cotton swabs, beddings (for example, pillow cases, sheets, futon covers, cotton in pillows or futons and the like), interior products (for example, curtains, shoji, sofa covers, doormats, cotton in cushions and the like), and kitchen/bath/toilet products (for example, wet tissue, toilet seat covers, toilet mats, bath mats, kitchen mats and the like).

(G) Purpose of Stabilization

The term "stabilization" refers to prevent degradation or degeneration of a substance which is unstable alone and degraded or degenerated. By making clathrate of the substance which is unstable alone, the substance is stabilized and can be store for a long period as compared with the substance alone. Examples of a guest substance to be made clathrate with the amylose-containing rayon fibers for this purpose include those which are easily degraded by light, ultraviolet, heat, oxygen or the like, and can be made clathrate with amylose.

Examples of the guest substances are as described in the above (d) of (1.3).

Specific examples of products include medical patches, colorfast fabric products and the like.

(H) Purpose of Sustained Release

The term "sustained release" means to release a substance gradually. Examples of a guest substance to be made clathrate with the amylose-containing rayon fibers for this purpose are as described in the above (e) of (1.3).

Specific examples of products include hygienic goods (masks, gloves, aprons, hats and caps, pillow cases, seat head covers, wet tissue, kitchen clothes, shoe inserts, shoe deodorants, clothes covers, and the like), building materials inside walls, wall papers, gauze, bandages, cotton swabs, beddings (pillow cases, sheets, futon covers, cotton in pillows or futon, and the like), interior products (curtains, shoji, sofa covers, doormats, cotton in cushions, etc.), and kitchen or bath or toilet products (wet tissue, toilet seat covers, toilet mats, bath mats, kitchen mats, and the like), insect proofing sheets, insect proofing mats, insect proofing curtains, insect proofing clothes, anti-molding sheets, anti-molding mats, anti-molding curtains, anti-molding clothing, and the like.

(I) Purpose of Ultraviolet Protection

The term "ultraviolet protection" means to reduce or eliminate the amount of ultraviolet. Examples of a guest substance to be made clathrate with the amylose-containing rayon fibers for this purpose include ultraviolet absorbing substances (also referred to as ultraviolet absorbing agents). Examples of the ultraviolet absorbing substances are as described in the above (f) of (1.3).

Specific examples of products include hats and caps with ultraviolet protection function, clothes with ultraviolet protection function, umbrellas with ultraviolet protection function, gloves with ultraviolet protection function, curtains with ultraviolet protection function, and the like.

(J) Purpose of Imparting of Cosmetic Functions

The term "imparting of cosmetic function" refers to providing such functions as moisturizing effect, whitening effect, anti-inflammatory effect, blood circulation promotion effect, antioxidative effect, anhidrotic action, refreshing effect, cell activating effect and the like, which are generally expected to be imparted to cosmetics. Examples of a guest substance to be made clathrate with the amylose-containing rayon fibers for this purpose include moisturizing components, whitening components, anti-inflammatory agents, cell activating agents, antioxidants, and the like. Examples of the moisturizing components, whitening components, anti-inflammatory agents, cell activating agents and antioxidants are as described in the above (g) of (1.3).

Specific examples of products include facemasks, poultices, bandages and the like.

(K) Purpose of Imparting of Medical Functions

The term "imparting of medical function" means to provide functions for a medical purpose. Examples of a guest substance to be made clathrate with the amylose-containing rayon fibers for this purpose include active ingredients of medicament, iodine and hair growers. Examples of the active ingredients of medicaments are as described in the above (d) of (1.3).

Specific examples of products include band-aids, gauze and clothing.

It is noted that while the purposes were separately described herein for convenience sake, it is natural that purposes may be sometimes overlapped.

(6. Concentrating, Recovery, Removal or Isolation of Iodine from Iodine-Containing Solution or Gas)

In the present specification, the term "iodine-containing solution" means a solution containing iodine or iodide ions. The iodide ions can be monovalent iodide ions or polyiodide ions. The polyiodide ion is preferably a triiodide ion, pentaiodide ion or hexaiodide ion. The iodine-containing solution can be any solution as long as the solution contains iodine. Examples of the iodine-containing solution include brine and iodine-containing industrial waste water. In the present specification, the term "brine" refers water whose salt concentration is higher than that of fresh water. Brine refers to, for example, sea water. The term "fresh water" refers water containing no salt. Brine is preferably brine obtained simultaneously when a natural gas is collected.

In one embodiment, the method of the present invention is a method for trapping iodine or polyiodide ions in fibers so as to concentrate, recover, remove or isolate the iodine or polyiodide ions, the method comprising the steps of: bringing amylose-containing rayon fibers into contact with iodine or polyiodide ions, thereby allowing an amylose in the amylose-containing rayon fiber to make a clathrate including the iodine or polyiodide ions.

In this method, for example, when the amylose-containing rayon fibers are brought into contacted with an iodine-containing solution, iodine or polyiodide ions contained in the iodine-containing solution are contacted with the amylose-containing rayon fibers, and as a result, the amylose of the amylose-containing rayon fibers are allowed to make a clathrate including the iodine or polyiodide ions.

It is preferred to use, as the amylose-containing rayon fibers, amylose-containing rayon fibers including no guest substance. The amylose rayon fibers can be used in any form. The amylose rayon fibers can be used, for example, in any form such as fibrous, filter, column and cotton forms.

The amylose-containing rayon fibers can be brought into contact with the iodine-containing solution by any method. For example, the amylose-containing rayon fibers are immersed in the iodine-containing solution or the iodine-containing solution is sprayed over the amylose-containing rayon fibers, or the iodine-containing solution is passed through amylose-containing rayon packed in a column or filter-shaped amylose-containing rayon.

It is also possible to allow amylose to make a clathrate including iodine by bringing the amylose-containing rayon fibers into contact with gaseous iodine. It is also possible to allow amylose to make a clathrate including iodine molecules by heating to the temperature enough to allow iodine to undergo sublimation while bringing the amylose-containing rayon into contact with an iodine powder (for example, mixing of the amylose-containing rayon with iodine in a container while warming). When the amylose-containing rayon is brought into contact with iodine, no use of a metal halide is preferable.

The content of the metal halide in the iodine clathrate amylose-containing rayon obtained without using the metal halide is preferably about 0.1-fold molar or less, more preferably about 0.05-fold molar or less, particularly preferably about 0.01-fold molar or less, and most preferably about 0.001-fold molar or less, of the content of the iodine molecules ($I_2$). The metal halide is, for example, potassium iodide.

The time and temperature for bringing the amylose-containing rayon fibers into contact with iodine or polyiodide ions can be set arbitrarily. For example, when the amylose-containing rayon fibers are immersed in the iodine-containing solution, the temperature of the iodine-containing solution can be, for example, about 10° C. or higher, about 15° C. or higher, about 20° C. or higher, about 25° C. or higher, or the like. When the amylose-containing rayon fibers are immersed in the iodine-containing solution, the temperature of the iodine-containing solution can be, for example, about 40° C. or lower, about 30° C. or lower, about 25° C. or lower, about 20° C. or lower, or the like. When the amylose-containing rayon fibers are immersed in the iodine-containing solution, the immersion time can be, for example, about 5 minutes or more, about 10 minutes or more, about 20 minutes or more, about 30 minutes or more, about 40 minutes or more, about 50 minutes or more, about 60 minutes (1 hour) or more, about 2 hours or more, about 3 hours or more, about 4 hours or more, about 5 hours or more, about 6 hours or more, about 8 hours or more, about 12 hours or more, about 24 hours or more, or the like. The heating time can be, for example, about 1 week or less, about 3 days or less, about 2 days or less, about 1 day (24 hours) or less, about 18 hours or less, about 16 hours or less, about 14 hours or less, about 12 hours or less, about 10 hours or less, about 8 hours or less, about 6 hours or less, about 5 hours or less, about 4 hours or less, about 3 hours or less, about 2 hours or less, about 1 hour or less, about 30 minutes or less, about 20 minutes or less, about 10 minutes or less, or the like.

The iodine or polyiodide ions included in a clathrate are eluted in water, for example, by immersing the iodine clathrate amylose-containing rayon fibers in water. By evaporating water from the resultant partially or completely, iodine is concentrated or purified. Since brine usually contains many salts, in addition to iodine, iodine is specifically concentrated by specifically allowing the amylose-containing rayon fibers to make a clathrate including the iodine, followed by elution in water or the like and further concentrating. It is noted that, in the present specification, the term "iodine" include both iodine molecules and iodide ions. However, "iodine" means iodine molecules in the case of the description of "iodine or polyiodide ions".

Increasing the concentration of iodine is referred to as "concentrating of iodine". For example, when iodine is taken out of the iodine-containing solution, and thus a solution containing iodine in higher concentration than that of the original iodine-containing solution is obtained, it can be said that iodine is concentrated.

Taking iodine out of once used water is referred to as "recovery of iodine".

When the amylose-containing rayon fibers are brought into contact with the iodine-containing solution, iodine is allowed to made a clathrate with amylose, and thus the iodine is removed from the iodine-containing solution. Therefore, the method of the present invention can be used for removal of iodine from the objective materials.

When the iodine-containing solution contains a plurality of substances, in addition to iodine, and these substances are substances that does not form a clathrate with amylose, only the iodine is allowed to included in a clathrate with amylose by bringing the amylose-containing rayon fibers into contact with the iodine-containing solution. Therefore, the method of the present invention can be used for isolation of iodine.

(7. Method of Allowing Amylose-Containing Rayon Fibers to Make a Clathrate Including Iodine)

By bring the amylose-containing rayon fibers into contact with iodine or polyiodide ions (and, optionally, other guest substances), the iodine or polyiodide ions can be included in a clathrate with the amylose-containing rayon fibers. Examples of the contact method include a method in which an iodine powder is stirred with the amylose-containing rayon fibers on a ball mill swivel; a method of a liquid phase contact in which the amylose-containing rayon fibers are immersed in a solution containing iodine or polyiodide ions (and optionally, other guest substances); a method of a vapor phase contact in which a solution containing iodine or polyiodide ions (and optionally, other guest substances) is sprayed over the amylose-containing rayon fibers, or vapor of iodine or polyiodide ions (and optionally, other guest substances) is contacted with the amylose-containing rayon fibers.

The content of the iodine in the iodine clathrate amylose-containing rayon is preferably about 0.01% by weight or more, more preferably about 0.05% by weight or more, particularly preferably about 0.1% by weight or more, and most preferably about 0.5% by weight or more. There is no particular upper limit on the content of the iodine in the iodine clathrate amylose-containing rayon as long as the content is a possible amount to be included in a clathrate. The content can be, for example, about 20% by weight or less, about 10% by weight or less, about 5% by weight or less, about 3% by weight or less, about 2% by weight or less, about 1.5% by weight or less, or the like.

EXAMPLES

The present invention will be described below by way of Examples, but the present invention is not limited thereto.

Methods for evaluation test used in Examples and Comparative Examples are as follows.

Synthetic Example 1

Synthesis of Amylose

Thermostabilized glucan phosphorylase derived from potato tuber, prepared and purified according to the method described in Example 2-1A in International Publication No. WO 2004/113525 pamphlet (glucan phosphorylase with the amino acid sequence of SEQ ID NO: 34 described in International Publication No. WO 2004/113525 pamphlet; 1 unit/mL), and thermostabilized sucrose phosphorylase derived from $Streptococcus$ $mutans$, prepared according to the method described in Example 2A in International Publication No. WO 2005/24008 pamphlet (sucrose phosphorylase with the amino acid sequence of SEQ ID NO: 22 described in International Publication No. WO 2005/24008 pamphlet; 1 unit/mL) were added to a reaction liquid (1 Liter) containing 20 mM phosphate buffer (pH 7.0), 20 g/L of sucrose and various concentrations of a malto-oligo saccharide mixture (3,880, 232, 77, 44 or 8.8 mg/L), and this was incubated at 37° C. for 16 hours. After completion of the reaction, the weight average molecular weight (Mw), degree of polymerization, and polydispersity (Mw/Mn) of the generated α-1,4-glucan were determined. The respective results are shown in Table 1 below.

TABLE 1

| Samples | Malto-oligo saccharide mixture (mg/L) | Mw (kDa) | Degree of Polymerization | Polydispersity (Mw/Mn) |
| --- | --- | --- | --- | --- |
| 1 | 3880 | 5.2 | 32 | 1.12 |
| 2 | 232 | 46.2 | 285 | 1.15 |
| 3 | 77 | 117.4 | 725 | 1.02 |
| 4 | 44 | 281.0 | 1735 | 1.01 |
| 5 | 8.8 | 780.5 | 4818 | 1.01 |

According to Table 1, amyloses with the degree of polymerization ranging from 32 to 4,818 (Mw 5.2 to 780.5 kDa) were obtained by changing the concentration ratio of sucrose to primer (i.e., malto-oligo saccharide mixture). The polydispersities (Mw/Mn) of amylose in all of these samples were 1.2 or less.

<1. Measurement of Weight Average Molecular Weight of Amylose>

The molecular weight of glucans, which was synthesized in Synthetic Example 1 and used in the present invention, were measured according to the following method.

The glucan synthesized in Synthetic Example 1 was completely dissolved with 1N sodium hydroxide, and neutralized with an appropriate amount of hydrochloric acid. The obtained glucan (about 300 μg) was subjected to gel filtration chromatography, whose device was equipped with both differential refractometer and multi-angle light scattering detector, and the average molecular weight thereof was determined.

Specifically, Shodex SB806M-HQ (manufactured by Showa Denko K.K.) used as a column, a multi-angle light scattering detector (DAWN-DSP manufactured by Wyatt Technology Corporation) and differential refractometer (Shodex RI-71 manufactured by Showa Denko K.K.) used as detectors, were used in connected in this order. The column temperature was maintained at 40° C., and a 0.1M sodium nitrate solution was used as an eluant at a flow rate of 1 mL/minute. The weight average molecular weight was determined by collecting the obtained signals using a data analysis software (trade name ASTRA, manufactured by Wyatt Technology Corporation) and analyzing the obtained signals using the same software.

Examples 1-1 to 1-4 and Comparative Examples 1-1 to 1-4

Production of Amylose-Containing Rayon Fiber

Viscose was prepared from a raw material pulp (LDPT manufactured by Nippon Paper Chemicals Co., Ltd.) according to a conventional method. In this viscose, the cellulose content was 9% by weight, the alkaline content was 5% by weight, and the falling ball viscosity was 60 seconds.

Each of the enzymatically synthesized amylase having an average molecular weight of $5.2 \times 10^3$, $4.62 \times 10^4$ or $1.174 \times 10^5$ (containing no branch structure), prepared in Synthetic Example 1, was dissolved in an aqueous 5% by weight NaOH solution, to prepare an aqueous alkaline solution of amylose. Any of these aqueous alkaline solutions and viscose were mixed according to a conventional method, followed by spinning, to give amylose-containing rayon fibers. Control rayon fibers were obtained by spinning the viscose alone, without mixing it with the aqueous alkaline solution (Comparative Example 1-1). Wherein, amylose was charged in the amylose-containing rayon fibers wherein the quantitative ratio (weight ratio) of the amylose to the cellulose are changed as shown in Table 2 below by changing the mixing proportion of the aqueous alkaline solution to the viscose.

On the other hand, in the case of using amylose having an average molecular weight of $2.810 \times 10^5$ or $7.805 \times 10^5$ synthesized in Synthetic Example 1, it was failed to produce an aqueous alkaline solution of amylose suitable for the production of the objective rayon, and thus failed to synthesize rayon fibers. The reasons were because uniform dissolution was difficult even though the concentration of amylose was 5%, and even though the dissolution was successful, viscosity of the obtained alkaline solution of amylose was high, which made it difficult to be mixed with the viscose liquid uniformly, and the like. Especially, the fact that it was failed to produce rayon using amylose having an average molecular weight of $2.810 \times 10^5$, which is an enzymatically synthesized amylose having a molecular weight of 500,000 or less, was characteristic to the enzymatically synthesized amylose and was unexpected.

The amylose contents in the amylose-containing rayon fibers and the control rayon fibers were quantified according to the following method. The amylose-containing rayon fibers or the control rayon fibers, the amount of which was 20 mg, were dissolved in a copper ammonia solution, and neutralized and diluted simultaneously with an acetic acid solution (2 mL in total), to reprecipitate only cellulose. It was subjected to centrifuge at 13,200×g for 10 minutes. The amount of the amylose in the supernatant was quantified according to a phenol-sulfuric acid method. The results are shown in Table 2.

TABLE 2

Amount of amylose charged and content of amylose in the obtained rayon fibers

| Kind | | Amount of amylose charged (%) | Measured value of content of amylose (%) |
|---|---|---|---|
| Comparative Example 1-1 | None | 0 | 0 |
| Comparative Example 1-2 | Amylose (Average molecular weight: $5.2 \times 10^3$) | 5 | 0.4 |
| Comparative Example 1-3 | Amylose (Average molecular weight: $5.2 \times 10^3$) | 20 | 0.9 |
| Example 1-1 | Amylose (Average molecular weight: $4.62 \times 10^4$) | 5 | 3.1 |
| Example 1-2 | Amylose (Average molecular weight: $4.62 \times 10^4$) | 20 | 11.6 |
| Example 1-3 | Amylose (Average molecular weight: $1.174 \times 10^5$) | 5 | 1.8 |
| Example 1-4 | Amylose (Average molecular weight: $1.174 \times 10^5$) | 20 | 11.6 |

Amount charged (%) = {(weight of amylose) × 100}/(total weight of cellulose + amylose)

As is shown in the results of Table 2, the content of amylose having an average molecular weight of $5.2 \times 10^3$ was extremely low in the rayon. The results revealed that almost all of added amount of amylose having an average molecular weight of $5.2 \times 10^3$ hardly remained in the rayon, while amylose having a molecular weight of $4.62 \times 10^4$ or more could be included in the rayon.

Example 2

Evaluation on Ability of Amylose-Containing Rayon Fibers to Form a Clathrate

The ability of the amylose-containing rayon fibers produced in Examples 1-1 to 1-4 to form a clathrate and the ability of the control rayon fibers produced in Comparative Examples 1-1 to 1-3 to form a clathrate were measured using nonyl phenol as a guest substance.

The amylose-containing rayon fibers produced in Examples 1-1 to 1-4 and the control rayon fibers produced in Comparative Examples 1-1 to 1-3 were respectively impregnated with nonyl phenol by immersing 50 mg of each rayon fibers in 3 mL of an aqueous 50% methanol solution containing nonyl phenol in a concentration of 100 ppm at 25° C. for 3 hours. The concentration of nonyl phenol in the aqueous solution was measured on liquid chromatography before and after immersion of the rayon fibers.

The conditions of liquid chromatography were as follows. TSKgel ODS-100Z (manufactured by TOSOH CORPORATION) was used as a column, a UV detector SPD-6A (manufactured by Shimadzu Corporation) was used as a detector, and LC-6A (manufactured by Shimadzu Corporation) was used as a feed pump. The column temperature was maintained at 40° C., and 80% methanol was used as an eluant at a flow rate of 1.0 mL/minute.

The ability to form a clathrate was evaluated by the ratio of adsorption of nonyl phenol to rayon determined by the following equation.

[Equation 4]

$$\text{Ratio of adsorption of nonyl phenol to rayon (\%)} =$$
$$100 - (\text{recovery ratio of nonyl phenol (\%)})$$

$$\text{Recovery ratio of nonyl phenol (\%)} =$$
$$100 \times \left\{ \frac{\begin{array}{c}(\text{concentration of nonyl} \\ \text{phenol after immersion of rayon})\end{array}}{\begin{array}{c}(\text{concentration of nonyl} \\ \text{phenol before immersion of rayon})\end{array}} \right\}$$

The ability of the amylose-containing rayon fibers to form a clathrate (%) was calculated based on Equation 3 described above. In other words, it was calculated by subtracting the nonyl phenol adsorption ratio of the control rayon fibers from the nonyl phenol adsorption ratio of the amylose-containing rayon fibers. The results are shown in Table 3.

TABLE 3 ability of rayon fibers to form a clathrate including nonyl phenol

| Kind | | Amount of amylose charged (%) | Ratio of adsorption of nonyl phenol to rayon fibers (%) | ability of rayon fibers to form a clathrate (%) |
|---|---|---|---|---|
| Comparative Example 1-1 | None | 0 | 5.1 | — |
| Comparative Example 1-2 | Amylose (Average molecular weight: $5.2 \times 10^3$) | 5 | 5.6 | 0.5 |
| Comparative Example 1-3 | Amylose (Average molecular weight: $5.2 \times 10^3$) | 20 | 6.4 | 1.3 |
| Example 1-1 | Amylose (Average molecular weight: $4.62 \times 10^4$) | 5 | 9.2 | 4.1 |
| Example 1-2 | Amylose (Average molecular weight: $4.62 \times 10^4$) | 20 | 13.1 | 8.0 |
| Example 1-3 | Amylose (Average molecular weight: $1.174 \times 10^5$) | 5 | 12.1 | 7.0 |
| Example 1-4 | Amylose (Average molecular weight: $1.174 \times 10^5$) | 20 | 21.8 | 16.7 |

It was found that the rayon fibers containing amylose having an average molecular weight of $5.2 \times 10^3$ had almost no ability to form a clathrate, on the ground that the adsorption ratio of the rayon fibers containing amylose having an average molecular weight of $5.2 \times 10^3$ toward nonyl phenol in Comparative Examples 1-2 and 1-3 was almost equal to that of the control rayon in Comparative Example 1-1, and that their ability to form a clathrate was as low as 1.3% or less. In contrast, it was found that the amylose-containing rayon in Examples 1-1 to 1-4 presented the adsorption ratio 1.8 to 4.3 times higher than that in Comparative Example 1-1, and these amylose-containing rayon had high ability to form a clathrate of 4.1% to 16.7%. The ability to form a clathrate increased in accordance with the increase of the amount of amylose to be blended and the increase of the molecular weight of amylose.

As is shown in Table 2, the amylose content in Example 1-2 and 1-4 were almost same. However, the ability to form a clathrate including nonyl phenol was about 2.1 times higher in the rayon containing amylose of $1.174 \times 10^5$ than in the rayon containing amylose of $4.62 \times 10^4$. This revealed that the ability of amylose in rayon to form a clathrate is largely influenced by the molecular weight of amylose, in addition to the content.

Considering the fact that amylose having an average molecular weight of $2.810 \times 10^5$ or more was failed to be contained in the rayon fibers, it was revealed that the average molecular weight of amylose needed to be more than $5.2 \times 10^3$ and less than $2.810 \times 10^5$ in order to produce rayon fibers containing amylose capable of exerting the ability to form a clathrate including nonyl phenol.

Example 3

Measurement of Amount of Iodine Included in a Clathrate with Amylose-Containing Rayon Fibers The amount of iodine included in a clathrate with the amylose-containing rayon fibers produced in Examples 1-1 to 1-4 and that included in a clathrate with the control rayon fibers produced in Comparative Examples 1-1 and 1-3 were measured.

The amount of iodine included in a clathrate was evaluated by the following method. The amylose-containing rayon fibers or control rayon fibers (1 g) and 60 mL of an iodine solution (iodine composition ratio: $I_2$: $I^-$=1:4, concentration of iodine solution [total iodine concentration: 610 ppm in Comparative Example 1-2, 945 ppm in Comparative Example 1-3, 2,265 ppm in Example 1-1, 7,893 ppm in Example 1-2, 1,431 ppm in Example 1-3 and 7,893 ppm in Example 1-4]) were placed in a screw neck flask, stirred at a rotation rate of 130 rpm for 13 hours. Then, the sample was taken out, and subjected to suction filtration. Next, the sample was immersed and stirred in 100 mL of pure water for 5 minutes, removed from the pure water, and subjected to suction filtration. This procedure was repeated 3 times. Then, the sample was dried in a desiccator at room temperature. Through these steps, iodine was allowed to be included in a clathrate with the amylose-containing rayon fibers or the control rayon fibers.

The iodine content in the amylose-containing rayon fibers or the control rayon fibers was measured as follows after the iodine clathrate treatment. The amylose-containing rayon fibers or control rayon fibers (50 mg) after the iodine clathrate treatment was suspended in 50 mL of water. A solution containing bromine, potassium acetate and acetic acid (bromine: 4 mL+ potassium acetate: 100 g+acetic acid: 1,000 mL) (10 mL) was added to the suspension liquid, and left to stand for 10 minutes. Formic acid (3 mL) was added, and left to stand for 5 minutes. Then, potassium iodide (0.5 g) was added, and the generated $I_2$ component was titrated with an aqueous 0.01M sodium thiosulfate solution, to obtain the total iodine concentration of the suspension liquid and calculate the total iodine content. The amount of iodine included in a clathrate based on the theoretical value was calculated by setting the maximum amount of iodine included in a clathrate with amylose (20% of amylose weight) as 100%. The results are shown in Table 4.

TABLE 4

Amount of amylose charged, amount of iodine included in a clathrate, amount of iodine included in a clathrate based on theoretical value

| Kind | | Amount of amylose charged (%) | Amylose content (%) | Amount of iodine included in a clathrate (%) | Amount of iodine included in a clathrate based on theoretical value *[1] (%) |
|---|---|---|---|---|---|
| Comparative Example 1-1 | None | 0 | 0 | 0 | 0 |
| Comparative Example 1-2 | Amylose (Average molecular weight: $5.2 \times 10^3$) | 5 | 0.4 | 0.005 | 6.3 |
| Comparative Example 1-3 | Amylose (Average molecular weight: $5.2 \times 10^3$) | 20 | 0.9 | 0.006 | 3.3 |
| Example 1-1 | Amylose (Average molecular weight: $4.62 \times 10^4$) | 5 | 3.1 | 0.072 | 11.6 |
| Example 1-2 | Amylose Average molecular weight: $4.62 \times 10^4$) | 20 | 11.6 | 0.923 | 39.8 |
| Example 1-3 | Amylose (Average molecular weight: $1.174 \times 10^5$) | 5 | 1.8 | 0.126 | 35.0 |
| Example 1-4 | Amylose (Average molecular weight: $1.174 \times 10^5$) | 20 | 11.6 | 1.341 | 57.8 |

*[1] Amount of iodine included in a clathrate based on theoretical value (%) = 100 × (amount of iodine included in a clathrate)/{(amylose content) × 0.2}

It was found that the rayon fibers containing amylose having an average molecular weight of $5.2 \times 10^3$ had an amount of iodine included in a clathrate based on the theoretical value of 7% or less, and hardly made iodine included in a clathrate. In contrast, it was found that the amylose-containing rayon fibers having an average molecular weight of $4.62 \times 10^4$ or $1.174 \times 10^5$ can allow iodine to be included in a clathrate, in an amount of iodine included in a clathrate based on the theoretical values of 10% or more. The amount included in a clathrate based on the theoretical value increased in accordance with the increase of the amount of amylose to be blended and the increase of the molecular weight of amylose.

Example A

Stability Test of Iodine Clathrate Amylose-Containing Rayon Fibers

Air which was dried by passing through activated carbon was fed at 0.5 L/minute for 120 hours to a glass column (inside diameter of 10 mm) filled with the amylose-containing rayon fibers produced in Example 1-2 after subjected to iodine clathrate treatment in Example 3 (500 mg). It is noted that the aeration test was carried out in a thermostatic chamber at 40° C. A gas washing bottle charged with 200 mL of an aqueous 0.01M sodium hydroxide solution was connected to the column outlet, to absorb iodine released from the iodine clathrate amylose-containing rayon fibers. The amounts of iodine in the absorption liquid (aqueous sodium hydroxide solution after absorption of iodine) and in the iodine clathrate amylose-containing rayon fibers after 48 hours and 120 hours air feeding were measured in the same manner as in Example 3. The results are shown in Table 4A. It is noted that the expression "Amount of iodine (mg) in iodine clathrate amylose-containing rayon fibers" in Table 4A is the amount of iodine contained in 500 mg of the iodine clathrate amylose-containing rayon used for the aeration test.

TABLE 4A

Evaluation of stability of iodine clathrate amylose-containing rayon by aeration test

| Aeration period of time (h) | Amount of iodine released from iodine clathrate amylose-containing rayon (mg) | Amount of iodine in iodine clathrate amylose-containing rayon (mg) | Iodine remaining ratio (%) |
|---|---|---|---|
| 0 | 0 | 4.610 | 100 |
| 48 | 0.056 | 4.554 | 98.8 |
| 120 | 0.070 | 4.540 | 98.4 |

Thus, it was found that the amylose-containing rayon fibers could stably retain iodine.

Example B

Stability Test of Iodine Clathrate Amylose-Containing Rayon Fibers (Influence of Potassium Iodide)

The amylose-containing rayon fibers (1 g) having an average molecular weight of $1.174 \times 10^5$ in Example 1-4 and 24.2 mg of an iodine powder were placed in a 50 mL screw vial, and stirred on a ball mill swivel) in a dryer set at 50° C. for 48 hours. Heating in a thermostatic chamber at 50° C. accelerates sublimation of iodine molecules, and the sublimated iodine molecules are allowed to be included in a clathrate with the amylose in the rayon fibers. Then, the rayon fibers after clathrate treatment was taken out of the screw vial, placed in a 40° C. thermostatic chamber, and fed with air, which had been dried with activated carbon, at 0.5 L/minute for 93 hours. As a result, excessive iodine was removed from the rayon fibers, to give iodine clathrate amylose-containing rayon fibers containing no potassium iodide. As these rayon fibers had not been brought to contact with potassium iodide at the production stage, it does not contain potassium iodide.

The iodine clathrate amylose-containing rayon fibers (500 mg) containing no potassium iodide was charged in a glass column (inside diameter of 10 mm), and air which had been dried by passing through activated carbon was fed at 0.5 L/minute for 120 hours to this glass column. It is noted that the aeration test was carried out in a thermostatic chamber at 40° C. A gas washing bottle charged with 200 mL of an aqueous 0.01M sodium hydroxide solution was connected to the column outlet, to absorb iodine released from the iodine clathrate amylose-containing rayon fibers. The amounts of iodine in the absorption liquid (aqueous sodium hydroxide solution after absorption of iodine) and in the iodine clathrate amylose-containing rayon fibers after 48 hours air feeding and 120 hours air feeding were measured in the same manner as in Example 3. The results are shown in Table 4B. It is noted that the expression "Amount of iodine (mg) in iodine clathrate amylose-containing rayon fibers" in Table 4B is the amount of iodine contained in 500 mg of the iodine clathrate amylose-containing rayon used for the aeration test. The amount of iodine included in a clathrate in the iodine clathrate amylose-containing rayon was 1.39% by weight when the air feeding time was 0 hour, and the amount of iodine included in the clathrate was 59.9% based on the theoretical value.

TABLE 4B

Stability test of iodine clathrate amylose-containing rayon which contains no potassium iodide by aeration test

| Aeration period of time (h) | Amount of iodine released from iodine clathrate amylose-containing rayon (mg) | Amount of iodine in iodine clathrate amylose-containing rayon (mg) | Iodine remaining ratio (%) |
|---|---|---|---|
| 0 | 0 | 6.95 | 100 |
| 48 | 0.32 | 6.63 | 95.3 |
| 120 | 0.35 | 6.60 | 95.0 |

Thus, it was found that the amylose-containing rayon fibers could stably retain iodine without potassium iodide. This leads to the conclusion that the amylose-containing rayon fibers do not require metal halide such as potassium iodide, in order to retain iodine stably.

Example 4

Washing Test of Amylose-Containing Rayon Fibers

The amylose-containing rayon fibers produced in Examples 1-2 and 1-4 or the control rayon fibers produced in Comparative Examples 1-1 and 1-3 were subjected to a washing test, to confirm the stability of amylose in the amylose-containing rayon fibers.

In details, 50 mg of each of the rayon fibers was soaked in water or a solution of a commercially available enzyme-containing detergent (TOP, manufactured by LION Corporation) adjusted to the concentration of 0.75 mg/mL for 3 hours. Next, the fibers were placed in a 2 mL centrifugal filtration filter (5 μm) to be subjected to centrifugal filtration at 12,000×g for 4 minutes, and the solution was recovered. In order to measure the amount of amylose eluted in the recovered filtrate, the following operation was carried out. The filtrate of the rayon fibers washed with water was diluted 3 times with water, and glucoamylase (18 U/mL) and α-amylase (2.6 U/mL) were allowed to act on this. The filtrate of the rayon washed with the detergent was diluted three times with an aqueous 1% acetic acid solution to neutralize it, and glucoamylase (18 U/mL) and α-amylase (2.6 U/mL) were allowed to act on this. Due to the actions of glucoamylase and α-amylase, amylose was converted into glucose. The amount of glucose was quantified using a glucose quantification kit (manufactured by Wako Pure Chemical Industries, Ltd.), and the quantitative value was multiplied by the dilution fold to give the concentration of amylose. The results are shown in Table 5.

TABLE 5

Results of washing test

| Kind of amylose | Amount of amylose charged (%) | Amylose content (%) | Amount of amylose eluted after washing with water[*1] (%) | Amount of amylose eluted after washing with detergent[*2] (%) |
|---|---|---|---|---|
| Comparative Example 1-1 | None | 0 | 0 | 0 | 0 |
| Comparative Example 1-3 | Amylose (Average molecular weight: $5.2 \times 10^3$) | 20 | 0.9 | 0.17 | 0.18 |
| Example 1-2 | Amylose (Average molecular weight: $4.62 \times 10^4$) | 20 | 11.6 | 0 | 0 |
| Example 1-4 | Amylose (Average molecular weight: $1.174 \times 10^5$) | 20 | 11.6 | 0 | 0 |

[*1]Amount of amylose (based on the weight of rayon, %) eluted from rayon after washing with water
[*2]Amount of amylose (based on the weight of rayon, %) eluted from rayon after washing with detergent
Amount of amylose eluted (%) = 100 × (amylose concentration (mg/mL))/(amount of detergent liquid added (mL))

In the rayon fibers containing amylose having an average molecular weight of $5.2 \times 10^3$, elution of a small amount of amylose was found. In contrast, in the rayon fibers containing amylose of $4.62 \times 10^4$ and the rayon fibers containing amylose of $1.174 \times 10^5$, elution of amylose due to washing was not found at all.

Example 5

Production of Nonwoven Fabric Filter of Amylose-Containing Rayon

The rayon fibers containing amylose having an average molecular weight of $1.174 \times 10^5$ (charged amount of 20%) produced in Example 1-4 was processed into nonwoven fabric about 3 mm in thickness by a needle punching method, to give a nonwoven fabric of amylose-containing rayon. The nonwoven fabric was cut into a disk shape 7 cm in diameter, to give a nonwoven fabric filter of amylose-containing rayon (Example 5).

Example 6

Production of Nonwoven Fabric Filter of Iodine Clathrate Amylose-Containing Rayon The nonwoven fabric filter of amylose-containing rayon (disk shape 7 cm in diameter) produced in Example 5 was placed in a petri dish filled with a 5 mM iodide solution, and iodine was impregnated. After impregnation, the filter was subjected to suction filtration, washed with a 5 mM potassium iodide solution, and subjected to suction filtration once again. This washing operation was repeated three times. After air drying, a nonwoven fabric filter of iodine clathrate amylose-containing rayon (Example 6) was obtained.

Example 7

Stability of Nonwoven Fabric Filter of Iodine Clathrate Amylose-Containing Rayon The X-ray fluorescence intensity of the nonwoven fabric filter of iodine clathrate amylose-containing rayon produced in Example 6 was measured by a X-ray fluorescence measurement method. Since X-ray fluorescence is proportional to the amount of iodine, the stability of iodine in the filter can be evaluated by examining the transition of the X-ray fluorescence intensity. When the X-ray fluorescence intensity of iodine in the nonwoven fabric of iodine clathrate amylose-containing rayon was observed for 47 days, it was found that the iodine in the nonwoven fabric was diminishing at a quite slow speed, as shown in FIG. 1. Thus, it was revealed that the nonwoven fabric of amylose-containing rayon could stably retain iodine.

Example 8

Figure 2:
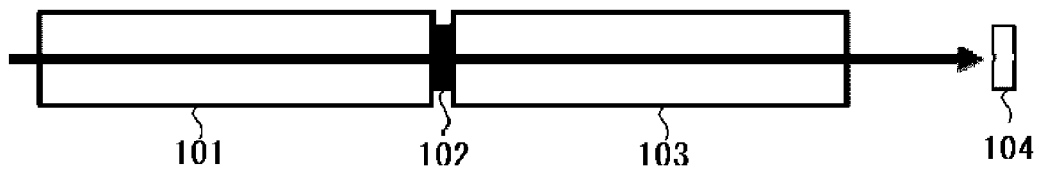
FIG. 2 is a schematic view of a device used in Example 8. It shows a cross sectional view of the device in the longitudinal axis. Holders 101 and 103 are cylindrically-shaped, and a test piece 102 is interposed between the holders 101 and 103. The arrow indicates the route of an influenza virus solution. The influenza virus solution sprayed passes through the holder 101, test piece 102 and holder 103, and then collected in a gelatin filter 104.

Test for Virus Inactivation by Passing Through Nonwoven Fabric Filter of Iodine Clathrate Amylose-Containing Rayon The test for virus inactivation by passing through a filter was carried out by measuring the infectivity titer of a virus after allowing the virus to passing through the nonwoven fabric filter of iodine clathrate amylose-containing rayon produced in Example 6. In details, the nonwoven fabric filter of iodine clathrate amylose-containing rayon (test sample) produced in Example 6 or the nonwoven fabric filter of amylose-containing rayon (containing no iodine; control) produced in Example 5 was mounted between cylindrical holders (inside diameter of about 6 cm) 101 and 103 of a device shown in FIG. 2. The test was carried out by mounting one piece or four pieces of nonwoven fabric filter(s) (test sample) 102. A solution containing influenza viruses was sprayed over the nonwoven fabric filter(s) at 10 L/minute for 5 minutes using a nebulizer from one opening section of the device shown in FIG. 2. The viruses passed through the nonwoven fabric filter(s) were collected by a gelatin filter 104 mounted at an opening section at opposed side, and the virus infectivity titer was examined. The results of the test samples were compared to the results of controls. The results are shown in Table 6.

TABLE 6

Results of test for virus inactivation by passing through nonwoven fabric filter

| | Test samples | Infectivity titer of virus recovered |
|---|---|---|
| Comparative Example 8-1 | Nonwoven fabric filter of amylose-containing rayon containing no iodine (one piece) | $7.20 \times 10^4$ |
| Example 8-1 | Nonwoven fabric filter of iodine clathrate amylose-containing rayon (one piece) | $5.30 \times 10^3$ |
| Comparative Example 8-2 | Nonwoven fabric filter of amylose-containing rayon containing no iodine (four pieces) | $3.50 \times 10^3$ |
| Example 8-2 | Nonwoven fabric filter of iodine clathrate amylose-containing rayon (four pieces) | $6.30 \times 10^1$ |

In a comparison between Example 8-1 and Comparative Example 8-1, the only difference is in whether iodine is allowed to be included in a clathrate or not. Therefore, the virus inactivation by iodine can be evaluated by comparing the virus infectivity titer in Example 8-1 and that in Comparative Example 8-1. In a comparison between Example 8-2 and Comparative Example 8-2 as well, the virus inactivation by iodine can be evaluated. When comparing the cases where the nonwoven fabric filters of iodine clathrate amylose-containing rayon in Example 8-1 and 8-2 were used, and the cases where the nonwoven fabric filters of amylose-containing rayon containing no iodine in Comparative Example 8-1 and 8-2 were used, respectively, the infectivity titer of the viruses recovered was as low as about one fourteenth and one fifty-sixth, and therefore it was confirmed that there was a virus inactivation effect in the nonwoven fabric filters of iodine clathrate amylose-containing rayon.

Examples 9-1 through 9-3

Increase of Ability of Amylose-Containing Rayon Fibers to Form a Clathrate by Heat Treatment in Alcohols-Water Mixed Solution The amylose-containing rayon fibers (50 mg) produced in Example 1-4 and 3 mL of an aqueous solvent (aqueous 50 vol % methanol solution, aqueous 50 vol % ethanol solution or aqueous 50 vol % 1-propanol solution) were placed in a pressure-resistant glass test tube (10 mL), and the tube was sealed, and heated at 130° C. in a heat block for 30 minutes. The rayon fibers were taken out, subjected to suction filtration, heated at 50° C. in an oven for 2 hours for dryness, and cooled at room temperature to give heat-treated amylose-containing rayon fibers (aqueous 50% methanol solution: Example 5-1; aqueous 50% ethanol solution: Example 5-2; and aqueous 50% 1-propanol solution: Example 5-3). As was confirmed by Example 12 below, the ability of the amylose-containing rayon fibers to form a clathrate was improved by this heat treatment.

Examples 10-1 through 10-3

Increase of Ability of Amylose-Containing Rayon Fibers to Form a Clathrate by Heat Treatment after Alcohol Spray About 1 mL of methanol, ethanol or 1-propanol was sprayed over the amylose-containing rayon fibers (50 mg) produced in Example 1-4, and the fibers were sealed in a glass container, and the container was heated at 130° C. in an oven for 30 minutes, and left to stand at room temperature for cooling. It was then heated and dried at 50° C. in an oven for 2 hours, and left to stand at room temperature for cooling, to give amylose-containing rayon fibers treated with alcohol (methanol spray: Example 10-1, ethanol spray: Example 10-2, 1-propanol spray: Example 10-3). It is confirmed in the same manner as in Example 8 below that the ability of the amylose-containing rayon fibers to form a clathrate is improved by the alcohol treatment.

Example 11

Increase of Ability of Amylose-Containing Rayon Fibers to Form a Clathrate by Alkaline Treatment The amylose-containing rayon fibers (50 mg) produced in Example 1-4 was immersed in 3 mL of an aqueous 1N NaOH solution at room temperature for 1 hour, taken out, and added with an aqueous 1N hydrochloric acid solution for neutralization. It was taken out, washed with water, heated and dried at 50° C. in an oven for 2 hours, and then left to stand at room temperature for cooling, to give amylose-containing rayon fibers treated with alkali. It is confirmed in the same manner as in Example 12 below that the ability of the amylose-containing rayon fibers to form a clathrate is improved by the alkaline treatment.

Example 12

Evaluation on Ability of Amylose-Containing Rayon Fibers to Form a Clathrate Produced in Examples 9-1 Through 9-3>

In the evaluation of the ability to form a clathrate, nonyl phenol was used as a guest molecule.

The amylose-containing rayon fibers produced in Example 1-4, the amylose-containing rayon fibers treated in Example 9-1 through 9-3 or the control rayon fibers in Comparative Example 1-1, the amount of which was 50 mg, were immersed respectively in 3 mL of an aqueous 50% methanol solution, which contains nonyl phenol in a concentration of 100 ppm, at 25° C. for 15 hours, allowing nonyl phenol to be impregnated into the respective rayon fiber. The concentration of nonyl phenol in the aqueous solution was measured with liquid chromatography before and after immersion of the rayon fibers. The adsorption ratio of nonyl phenol to the rayon fibers and the ability of the rayon fibers to form a clathrate were obtained from the difference in the amount of nonyl phenol before and after immersion.

The conditions of liquid chromatography are as follows:
TSKgel ODS-100Z (manufactured by TOSOH CORPORATION) was used as a column, a UV detector SPD-6A (manufactured by Shimadzu Corporation) was used as a detector, and LC-6A (manufactured by Shimadzu Corporation) was used as a feed pump. The column temperature was maintained at 40° C., and 80% methanol was used as an eluant at a flow rate of 1.0 mL/minute. The results are shown in Table 7.

TABLE 7

| | ability of rayon fibers to form a clathrate including nonyl phenol | | |
|---|---|---|---|
| | Test samples | Ratio of adsorption of nonyl phenol to rayon fibers (%) *1 | ability of rayon fibers to form a clathrate (%) |
| Comparative Example 1-1 | Control rayon fibers | 4.6 | — |
| Example 1-4 | Untreated amylose-containing rayon fibers | 21.0 | 16.4 |
| Example 9-1 | Amylose-containing rayon fibers subjected to heat treatment in aqueous 50% methanol solution | 21.2 | 16.6 |
| Example 9-2 | Amylose-containing rayon fibers subjected to heat treatment in aqueous 50% ethanol solution | 27.4 | 22.8 |

TABLE 7-continued ability of rayon fibers to form a clathrate
including nonyl phenol

| Test samples | | Ratio of adsorption of nonyl phenol to rayon fibers (%) *1 | ability of rayon fibers to form a clathrate (%) |
|---|---|---|---|
| Example 9-3 | Amylose-containing rayon fibers subjected to heat treatment in aqueous 50% 1-propal solution | 29.1 | 24.5 |

*1 Ratio of adsorption of nonyl phenol to rayon (%) = 100 − (ratio of recovery of nonyl phenol (%)) *2
*2 Ratio of recovery of nonyl phenol (%) = 100 × {(nonyl phenol concentration after immersion of rayon)/(nonyl phenol concentration before immersion of rayon)}

It was found that the ability of the amylose-containing rayon fibers to form a clathrate was improved dramatically when the amylose-containing rayon fibers were subjected to heat treatment using an aqueous solution of alcohol having long alkyl chains.

Example 13

Microbiocidal Test Using Nonwoven Fabric Filter of Iodine Clathrate Amylose-Containing Rayon The microbiocidal effect of the nonwoven fabric filter of iodine clathrate amylose-containing rayon against *Escherichia coli* is examined. The iodine-containing nonwoven fabric filter or the control nonwoven fabric filter (containing no iodine) is brought to contact with a solution containing *Escherichia coli*. The solution is sampled over time, the samples are cultured, and then the number of *Escherichia coli* colonies is counted.

Example 14

Deodorization Test Using Nonwoven Fabric Filter of Iodine-Containing Amylose Rayon The nonwoven fabric filter of iodine-containing amylose rayon produced in Example 4 or the rayon nonwoven fabric filter (control) produced in Comparative Example 4 is placed in an airtight container containing a malodorous substance (nonenal, butyric acid, valeric acid or iso-valeric acid) and left to stand for 2 hours and 24 hours. Then, the amount of the malodorous substance contained in the air of the container is measured with gas chromatography before and after placing the nonwoven fabric filter in the container. These amounts are compared.

Example 15

Production of Deodorant-Containing Amylose Rayon Fibers

Iodine or polyiodide ions are used as an example of a guest molecule for a deodorant.

The rayon fibers containing amylose having an average molecular weight of $1.174 \times 10^5$ produced in Example 1-4 (charged amount of 20%) or the control rayon fibers (containing no amylose) produced in Comparative Example 1-1 are impregnated with a deodorant by immersing the rayon fibers in the deodorant solution for 1 hour. Then, the rayon fibers are taken out, and air-dried overnight at room temperature, to give a deodorant-containing amylose rayon.

The concentration of the deodorant in the deodorant solution is measured before and after immersion of rayon, in the same manner as in Example 2. The difference in the amounts of deodorant before and after impregnation is assumed to as an amount of the deodorant adsorbed in (making a clathrate within) the rayon. The results of Example are compared to those of control to evaluate the ability to form a clathrate.

Example 16

Concentrating, Recovery, Removal and Purification of Iodine Using Amylose Rayon Fibers The amylose rayon produced in Example 1-4 or the rayon (control) produced in Comparative Example 1-1 is placed in a bath containing iodine (for example, brine) and left to stand overnight. Then the rayon is taken out, washed, and subjected to pressurization and heating or steam distillation.

The objective chemical substance is concentrated and recovered.

Synthetic Example 2

Synthesis of Amylose

Thermostabilized glucan phosphorylase derived from potato tuber, prepared and purified according to the method described in Example 2-1A in International Publication No. WO 2004/113525 pamphlet (glucan phosphorylase with the amino acid sequence of SEQ ID NO: 34 described in International Publication No. WO 2004/113525 pamphlet; 1 unit/mL), and thermostabilized sucrose phosphorylase derived from *Streptococcus mutans*, prepared according to the method described in Example 2A in International Publication No. WO 2005/24008 pamphlet (sucrose phosphorylase with the amino acid sequence of SEQ ID NO: 22 described in International Publication No. WO 2005/24008 pamphlet; 1 unit/mL) were added to a reaction liquid (1 Liter) containing 20 mM phosphate buffer (pH 7.0), 20 g/L of sucrose and a malto-oligo saccharide mixture (245 mg/L), and this was incubated at 37° C. for 16 hours. After completion of the reaction, the weight average molecular weight (Mw), degree of polymerization, and polydispersity (Mw/Mn) of the generated α-1,4-glucan were determined. The results are shown in Table 8 below.

TABLE 8

| Samples | Malto-oligo saccharide mixture (mg/L) | Mw (kDa) | Degree of polymerization | Polydispersity (Mw/Mn) |
|---|---|---|---|---|
| 6 | 245 | 30.0 | 181 | 1.45 |

Examples 17-1 and 17-2

Production of Rayon Fibers Containing Amylose Having Average Molecular Weight of $3.00 \times 10^4$ Viscose was prepared from a raw material pulp (LDPT manufactured by Nippon Paper Chemicals Co., Ltd.) according to a conventional method. In this viscose, the cellulose content was 9% by weight, the alkaline content was 5% by weight, and the falling ball viscosity was 60 seconds.

The enzymatically synthesized amylose having an average molecular weight of $3.00 \times 10^4$ (containing no branch structure), prepared in the Synthetic Example 2, was dissolved in an aqueous 5% by weight NaOH solution, to prepare an aqueous alkaline solution of amylose. The aqueous alkaline solutions and viscose were mixed according to a conventional method, followed by spinning, to give amylose-containing rayon fibers. Wherein, amylose was charged in the amylose-containing rayon fibers wherein the quantitative ratio (weight ratio) of the amylose to the cellulose are changed as shown in Table 9 below by changing the mixing proportion of the aqueous alkaline solution to the viscose.

The amylose content in the amylose-containing rayon fibers was quantified according to the following method. The amylose-containing rayon fibers (20 mg) was dissolved in a copper ammonia solution, and neutralized and diluted simultaneously with an acetic acid solution (2 mL in total), to reprecipitate only cellulose. It was subjected to centrifuge at 13,200×g for 10 minutes. The amount of the amylose in the supernatant was quantified according to a phenol-sulfuric acid method. The results are shown in Table 9.

TABLE 9

Amount of amylose charged and content of amylose in the obtained rayon fibers

| Kind | | Amount of amylose charged (%) | Measure value of content of amylose (%) |
|---|---|---|---|
| Example 17-1 | Amylose (Average molecular weight: $3.00 \times 10^4$) | 5 | 2.9 |
| Example 17-2 | Amylose (Average molecular weight: $3.00 \times 10^4$) | 20 | 12.0 |

Amount charged (%) = {(weight of amylose) × 100}/(total weight of cellulose + amylose)

It was revealed from the results in Table 9 that amylose having an average molecular weight of $3.00 \times 10^4$ or more can be contained inside the rayon.

Example 18

Making a Clathrate of Nonyl Phenol with Amylose-Containing Rayon Fibers Produced in Examples 17-1 and 17-2

The clathrate forming ability of the rayon fibers containing amylose having an average molecular weight of $3.00 \times 10^4$, produced in Examples 17-1 and 17-2, was examined using nonyl phenol as a guest substance. The clathrate forming ability of the rayon fibers produced in Comparative Example 1-1 was also measured as a control. The method for making a clathrate including nonyl phenol and the method for evaluation of the clathrate forming ability were carried out in the same manner as in Example 2. The results are shown in Table 10.

TABLE 10 clathrate forming ability of rayon fibers containing amylose having an average molecular weight of $3.00 \times 10^4$

| Kind | | Amount of amylose charged (%) | Measured value of content of amylose (%) | Ratio of adsorption of nonyl phenol to rayon fibers (%) | clathrate forming ability of rayon fibers (%) |
|---|---|---|---|---|---|
| Comparative Example 1-1 | None | 0 | 0 | 4.8 | — |
| Example 17-1 | Amylose (Average molecular weight: $3.00 \times 10^4$) | 5 | 2.9 | 6.4 | 1.6 |
| Example 17-2 | Amylose (Average molecular weight: $3.00 \times 10^4$) | 20 | 12.0 | 7.8 | 3.0 |

As shown in Table 10, it was confirmed that the rayon fiber containing amylose having an average molecular weight of $3.00 \times 10^4$ in Examples 17-1 and 17-2 also had the clathrate forming ability. The clathrate forming ability thereof was lower than the results of Examples 1-1 through 1-4 in Table 3. It was confirmed that the molecular weight of amylose affected the clathrate forming ability, and the clathrate forming ability increased in accordance with the increase of molecular weight.

Example 19

Production of Thermal Bond Nonwoven Fabric of Amylose-Containing Rayon Fiber

The rayon fibers containing amylose having an average molecular weight of $1.174 \times 10^5$ produced in Example 1-4 (40% by weight) and polypropylene-polyethylene core sheath fibers (ES fibers manufactured by CHISSO CORPORATION) (60% by weight) were opened under air flow, mixed, webbed with a carding machine, and heated with a heat roll to produce a thermal bond nonwoven fabric (about 20 g/m$^2$) (Example 19).

Example 20

Clathrate of Iodine in Thermal Bond Nonwoven Fabric Blended with 40% Amylose-Containing Rayon Fiber Produced in Example 19

The thermal bond nonwoven fabric (1.7 g) blended with 40% by weight amylose-containing rayon fibers produced in Example 19 (17 cm×50 cm) was placed in a container which was charged with any of 200 mL aqueous iodine solution shown in Table 11, allowing iodine to be impregnated for about 10 seconds. It was subjected to centrifugation to remove excessive aqueous iodine solution, until the weight of the aqueous iodine solution impregnated in the nonwoven fabric became 2-3 times the weight of the nonwoven fabric. Then the nonwoven fabric was attached on a glass plate heated at 50° C. and then dried for 5 minutes, to give a iodine clathrate amylose-containing rayon nonwoven fabric.

In order to measure the iodine content in the nonwoven fabric, 5 mL of an aqueous 10 mM sodium thiosulfate solution was added to each nonwoven fabric (100 mg), and the resultant was left to stand for 1 hour with occasional stirring, allowing the entire iodine in the nonwoven fabric to be eluted as iodide ions ($I^-$). The solution was filtrated, and iodine in the solution was quantified with inductivity coupled plasma optical emission spectrometer SPS7700 manufactured by Seiko Instruments & Electronics Ltd.)). The iodine content (%) in the nonwoven fabric was calculated from the obtained results. The results are shown in Table 11.

TABLE 11

Iodine content of thermal bond nonwoven fabric blended with iodine clathrate amylose-containing rayon

| | Iodine solution used for impregnation | Iodine content in nonwoven fabric (% by weight) |
|---|---|---|
| Example 20-1 | Aqueous 0.087% iodine solution (Weight ratio: $I_2:I^- = 1:4$) | 0.49 |
| Example 20-2 | Aqueous 0.026% iodine solution (Weight ratio: $I_2:I^- = 1:4$) | 0.15 |
| Example 20-3 | Aqueous 0.013% iodine solution (Weight ratio: $I_2:I^- = 1:4$) | 0.08 |
| Example 20-4 | Aqueous 0.009% iodine solution (Weight ratio: $I_2:I^- = 1:4$) | 0.04 |
| Example 20-5 | Aqueous solution containing 0.056% of iodine and 40% of ethanol (Weight ratio: $I_2:I^- = 1:0$) | 0.06 |

Example 21

Stability of Thermal Bond Nonwoven Fabric Blended with 40% Iodine Clathrate Amylose-Containing Rayon Fibers Produced in Example 20-1

Five pieces of the iodine clathrate amylose-containing rayon nonwoven fabric produced in Example 20-1 were piled and fixed in a cylindrical holder of 12 cmφ in inside diameter, and to which air which have been dried by activated carbon was fed at 0.5 mL/minute. The test was carried out in a thermostatic chamber set at 40° C.

The air passed through the nonwoven fabric was guided to an absorption solution (aqueous 0.01M sodium hydroxide solution) so as to allow the solution to absorb iodine released in the air from the nonwoven fabric. Some of the absorption solution was sampled, a reducing agent (aqueous sodium sulfite solution) was added to the sample to convert the entire iodine absorbed into iodide ions, the iodide ions in the absorption solution was then measured by the ion chromatography method, and the amount of the iodine released was calculated.

Figure 3:
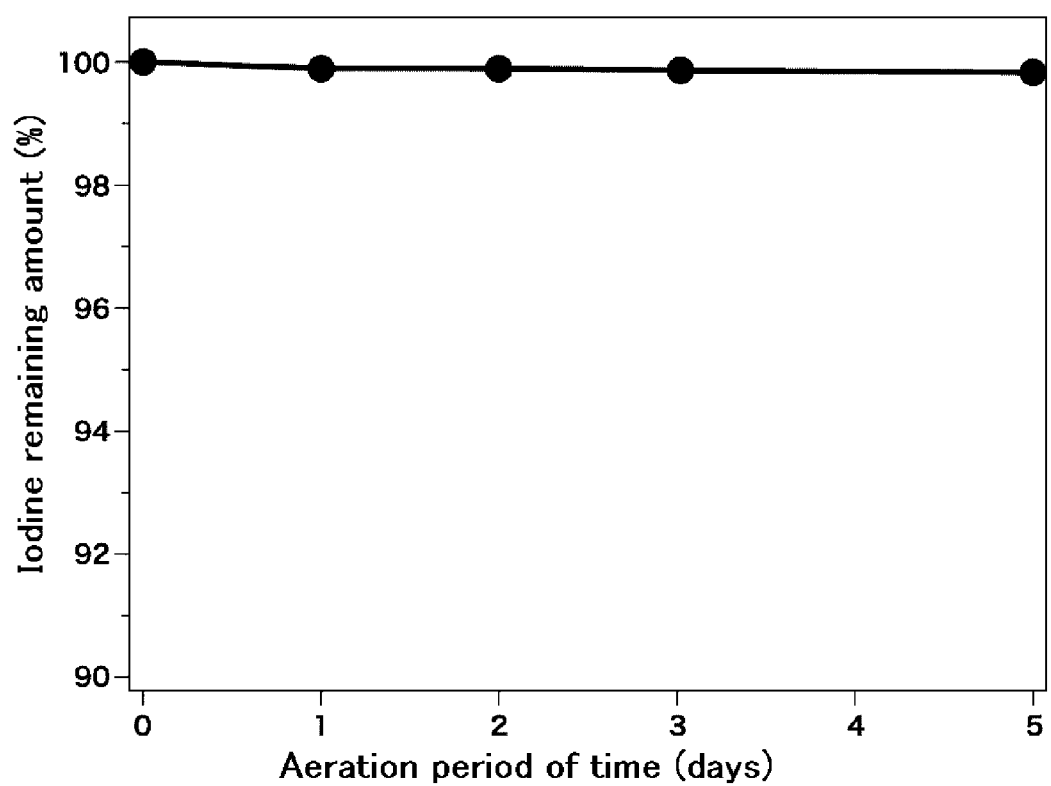
FIG. 3 is a graph showing a change of the residual amount of iodine in the iodine clathrate amylose-containing nonwoven rayon fabric over time.

The result is shown in FIG. 3. As shown in FIG. 3, the iodine clathrate amylose-containing rayon nonwoven fabric produced in Example 20-1 retained 99.8% of iodine even after dried air was fed at 40° C. for 5 days, and it was found that the fabric had high retaining stability of iodine.

Example 21B

Stability of Thermal Bond Nonwoven Fabric Blended with 40% Iodine Clathrate Amylose-Containing Rayon Fibers Produced in Example 20-1 (Influence of Humidity)

Five pieces of the iodine clathrate amylose-containing rayon nonwoven fabric produced in Example 20-1 were piled and fixed in a cylindrical holder of 12 cmφ in inside diameter, and to which the air whose relative humidity was adjusted to from 97 to 98% by allowing it to pass through a gas washing bottle with pure water was fed at 0.5 mL/minute. The test was carried out in a thermostatic chamber set at 40° C.

The air passed through the nonwoven fabric was guided to an absorption solution (aqueous 0.01M sodium hydroxide solution) so as to allow the solution to absorb iodine released in the air from the nonwoven fabric. Some of the absorption solution was sampled, iodide ions in the absorption solution were measured by the bromine method, and the amount of iodine released was calculated. The results are shown in Table 11B.

TABLE 11B

Iodine retaining stability test of iodine clathrate amylose-containing rayon nonwoven fabric by aeration using high humidity air

| Aeration period of time (hours) | Iodine remaining ratio (%) |
|---|---|
| 0 | 100 |
| 2 | 98.8 |
| 4 | 97.8 |
| 8 | 97.1 |
| 24 | 94.5 |

As shown in Table 11B, the iodine clathrate amylose-containing rayon nonwoven fabric produced in Example 20-1 retained 94.5% of iodine even after the air whose relative humidity was adjusted to from 97 to 98% was fed at 40° C. for 24 hours, it was found that the fabric had high retaining stability of iodine even under high humidity environments. Therefore, when used as, for example, a material for masks, the fabric can greatly reduce the risks against human safety.

Example 22

Virus Inactivation Test of Thermal Bond Nonwoven Fabric Blended with 40% Iodine Clathrate Amylose-Containing Rayon Fibers Produced in Examples 20-1 through 20-3

The inactivation test against influenza virus A was carried out on the thermal bond nonwoven fabrics (thermal bond nonwoven fabric blended with 40% iodine clathrate amylose-containing rayon) produced in Examples 20-1, 20-2 and 20-3. The thermal bond nonwoven fabric blended with 40% amylose-containing rayon produced in Example 19 was used as a control.

The test sample (100 mg) was placed in a 15 mL tube, and 100 μL of a virus liquid was brought into contact with the entire test sample. After a predetermined time, i.e., after 0 minute, 10 minutes, 30 minutes and 60 minutes of contact, 1.9 mL of a 0.3% sodium thiosulfate-containing phosphate buffer solution (PBS) was added to terminate the reaction. The liquid in the tube was recovered, and the virus infectivity titer ($TCID_{50}/mL$) was measured.

Figure 4:
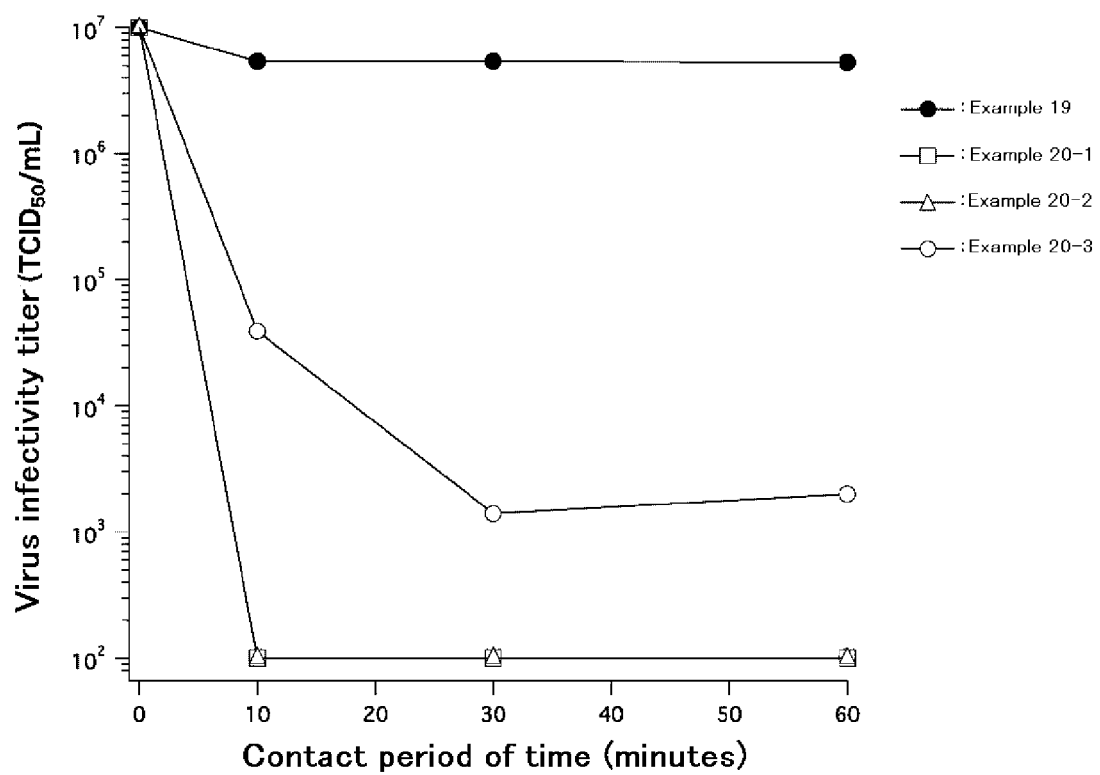
FIG. 4 is a graph showing inactivation of influenza virus A by the iodine clathrate amylose-containing nonwoven rayon fabric. The black circle denotes the result of Example 19, the white square denotes the result of Example 20-1, the white triangle denotes the result of Example 20-2, and the white circle denotes the result of Example 20-3.

The results are shown in FIG. 4. As shown in FIG. 4, any of the nonwoven fabrics in Examples 20-1, 20-2 and 20-3 exhibited an inactivation effect on influenza A. It was found from this that the amylose-containing rayon nonwoven fabric made a clathrate with 0.08% by weight or more of iodine exhibited an inactivation effect on influenza viruses A.

Example 23

Microbiocidal Test Against *Escherichia coli* and *Staphylococcus aureus* on Thermal Bond Nonwoven Fabric Blended with 40% Iodine Clathrate Amylose-Containing Rayon Fibers Produced in Examples 20-1 Through 20-5>

The microbiocidal test against *Escherichia coli* and *Staphylococcus aureus* was carried out on the thermal bond nonwoven fabrics produced in Examples 20-1 through 20-5 (thermal bond nonwoven fabric blended with 40% iodine clathrate amylose-containing rayon fibers). The thermal bond nonwoven fabric blended with 40% amylose-containing rayon produced in Example 19 was used as a control.

The colonies of *Escherichia coli* and *Staphylococcus aureus* grown on a plate medium were scraped with platinum loop in an amount of one platinum loop, inoculated into a culture fluid (*Escherichia coli*: LB medium; 1% TRYPTONE, 0.5% Yeast Extract, 0.5% NaCl. *Staphylococcus aureus*: nutrient medium; 0.3% meat extract, 0.5% PEPTONE), and subjected to shaking culture at 37° C. overnight. The concentration of the bacteria after the overnight culture was adjusted to 1 to $3 \times 10^8$ cfu/mL using a new culture fluid which has the same composition, and 50 µL thereof was added to 6 mL of a new culture fluid which is the same composition with above, followed by shaking culture at 37° C. for 3 hours. Since the culture fluid contained a component that inactivates iodine, an operation of bacterial collection was carried out next so as to remove the components of the culture fluid. The culture fluid was subjected to centrifugation (8,000 g, 4° C., 5 minutes), the supernatant fluid was discarded, and the bacteria was suspended once again with 6 mL of sterile saline and washed. The operation was performed 2 more times to remove the components of the culture fluid completely. The bacteria were diluted with the sterile saline until the bacterial concentration became $1.5 \times 10^5$ cfu/mL to prepare an inoculation bacterial liquid.

As described above, 5 kinds of the thermal bond nonwoven fabric blended with 40% iodine clathrate amylose-containing rayon fibers produced in Examples 20-1 through 20-5 were used as the test samples, and the thermal bond nonwoven fabric blended with 40% amylose-containing rayon fibers containing no iodine produced in Example 19 was used as a control.

The inoculation bacterial liquid (100 µL) adjusted to $1.5 \times 10^5$ cfu/mL was inoculated into 100 mg of the test sample so as to spread the liquid throughout the entire sample, and cultured at 37° C. for 1 hour. After the culture, elution of the bacteria from the test sample was carried out. Since a small amount of iodine may be eluted from the test sample at the time of bacterial elution, saline containing ascorbic acid, that inactivates iodine, was used. Saline containing 0.05% ascorbic acid (1,900 µL) after filter sterilization was added to the test sample after being cultured, to elute bacteria. A series of eluate dilutions were prepared, seeded over the plate media, and cultured at 37° C. The number of colonies was counted after 15 hours in the case of *Escherichia coli*, and after 48 hours in the case of *Staphylococcus aureus*. The dilution fold was multiplied by the number of colonies, and the viable bacterial count was determined. The results of the microbiocidal test are shown in Table 12.

TABLE 12

Microbiocidal effect of iodine clathrate amylose-containing rayon nonwoven fabric on *Escherichia coli* and *Staphylococcus aureus*

| Test sample | Iodine content (% by weight) | Viable bacterial count 1 hour after inoculation (number of cells) | |
|---|---|---|---|
| | | *Escherichia coli* | *Staphylococcus aureus* |
| Example 19 | 0 | $8.6 \times 10^3$ | $8.4 \times 10^3$ |
| Example 20-1 | 0.49 | less than 20 | less than 20 |
| Example 20-2 | 0.15 | less than 20 | less than 20 |
| Example 20-3 | 0.08 | less than 20 | less than 20 |
| Example 20-4 | 0.04 | less than 20 | $1.0 \times 10^2$ |
| Example 20-5 | 0.06 | less than 20 | less than 20 |

As shown in Table 12, it was found that all of the thermal bond nonwoven fabrics of the present invention had a bactericidal effect on *Escherichia coli* and *Staphylococcus aureus*. It was found from this that the thermal bond nonwoven fabric of the present invention, retaining iodine in an amount of 0.04% by weight or more, exerted extremely high bactericidal effect on *Escherichia coli* and *Staphylococcus aureus*.

As described above, the present invention has been exemplified using preferable embodiments of the present invention, but the present invention should not be construed so as to be limited to these embodiments. It is understood that the scope of the present invention should be construed only by claims. It is understood that those skilled in the art can carry out an equivalent scope based on the description of the present invention and common technical knowledge, from the description of specific preferable embodiments of the present invention. It is understood that the content of patents, patent applications and references cited in the present specification should be incorporated herein by reference, as if the content itself is specifically described in the present specification.

INDUSTRIAL APPLICABILITY

The present rayon fibers stably retains amylose, and does not substantially cause elution of amylose during an operation such as washing, and thus it is possible to endure repeated use. Furthermore, the present rayon fibers contain amylose in the state capable of exerting the clathrate function, and additional functions can be imparted to the fiber by adding various guest substances (especially, iodine or polyiodide ions). Use of this makes it possible to efficiently recover iodine or polyiodide ions from brine. Especially, the rayon fibers in which iodine or polyiodide ions being a clathrate exert quite excellent microbiocidal and deodorant functions.

The invention claimed is:

1. A method for producing an amylose-containing rayon fiber, comprising the steps of:
   mixing an aqueous alkaline solution of amylose with viscose to obtain a mixed liquid;
   spinning the mixed liquid to obtain an amylose-containing rayon fiber; and
   bringing the amylose-containing rayon fiber into contact with iodine or polyiodide ions, thereby allowing an amylose in the amylose-containing rayon fiber to make a clathrate including the iodine or polyiodide ions; wherein
   the amylose is an enzymatically synthesized amylose having a weight average molecular weight of $3 \times 10^4$ or more and $2 \times 10^5$ or less wherein said rayon fiber has the ability to form a clathrate of 1.6% to 24.5%.

2. The method according to claim 1, wherein the amylose-containing rayon fiber is subjected to a heating treatment and cooling treatment before bringing into contact with the iodine or polyiodide ions.

3. The method according to claim 1, wherein the amylose-containing rayon fiber is subjected to an alkaline treatment before bringing into contact with the iodine or polyiodide ions.

4. The method according to claim 1, wherein the enzymatically synthesized amylose is an amylose which does not contain a α-1,6-glucoside bond.

5. The method according to claim 1, wherein the enzymatically synthesized amylose has a polydispersity of 3.0 or less.

6. The method according to claim 1, wherein the content of the enzymatically synthesized amylose in the amylose-containing rayon fiber is 0.01% by weight or more and 50% by weight or less.

7. An amylose-containing rayon fiber, wherein amylose in the rayon fiber is not substantially eluted by washing and is dispersed in the rayon fiber in a state of exerting a clathrate action; and wherein the amylose is an enzymatically synthesized amylose having a weight average molecular weight of $3 \times 10^4$ or more and $2 \times 10^5$ or less, and the amylose includes iodine or polyiodide ions, wherein the rayon fibers have the ability to form a clathrate of 1.6% to 24.5%.

8. The amylose-containing rayon fiber according to claim 7, wherein the amylose is 0.01% by weight or more and 50% by weight or less.

9. The amylose-containing rayon fiber according to claim 7, wherein the enzymatically synthesized amylose is an amylose which does not contain an α-1,6-glucoside bond.

10. The amylose-containing rayon fiber according to claim 7, wherein the enzymatically synthesized amylose has a polydispersity of 3.0 or less.

11. The amylose-containing rayon fiber according to claim 7, further comprising a metal halide, wherein the metal halide is 0.1-fold moles or less of the iodine molecules ($I_2$).

12. A deodorant product comprising the amylose-containing rayon fiber, wherein amylose in the rayon fiber is not substantially eluted by washing and is dispersed in the rayon fiber in a state of exerting a clathrate action; and wherein the amylose is an enzymatically synthesized amylose having a weight average molecular weight of $3 \times 10^4$ or more and $2 \times 10^5$ or less, and the amylose includes iodine or polyiodide ions.

13. A antimicrobial product comprising the amylose-containing rayon fiber, wherein amylose in the rayon fiber is not substantially eluted by washing and is dispersed in the rayon fiber in a state of exerting a clathrate action; and wherein the amylose is an enzymatically synthesized amylose having a weight average molecular weight of $3 \times 10^4$ or more and $2 \times 10^5$ or less, and the amylose includes iodine or polyiodide ions.

14. A method for trapping iodine or polyiodide ions in a fiber so as to concentrate, recover, remove or isolate the iodine or polyiodide ions, the method comprising the steps of:
bringing an amylose-containing rayon fiber into contact with iodine or polyiodide ions, thereby allowing an amylose in the amylose-containing rayon fiber to make a clathrate including the iodine or polyiodide ions,
wherein the amylose-containing rayon fiber is obtained by a method comprising the steps of:
mixing an aqueous alkaline solution of amylose with viscose to obtain a mixed liquid; and
spinning the mixed liquid to obtain an amylose-containing rayon fiber; and
the amylose is an enzymatically synthesized amylose having a weight average molecular weight of $3 \times 10^4$ or more and $2 \times 10^5$ or less wherein said rayon fiber has the ability to form a clathrate of 1.6% to 24.5%.

15. A fabric comprising the amylose-containing rayon fiber according to claim 7.

16. A secondary processed article comprising the amylose-containing rayon fiber according to claim 7.

17. The amylose-containing rayon fiber according to claim 7, wherein the rayon fibers has ability to form a clathrate of 4.1% to 24.5%.

18. The amylose-containing rayon fiber according to claim 7, wherein the amylose-containing rayon fiber is produced by a method comprising dissolving amylose powder in an aqueous alkaline solution.

\* \* \* \* \*